United States Patent
Nakatsuchi et al.

(10) Patent No.: US 8,179,429 B2
(45) Date of Patent: May 15, 2012

(54) BODY-INSERTABLE APPARATUS AND BODY-INSERTABLE APPARATUS SYSTEM

(75) Inventors: Kazutaka Nakatsuchi, Hino (JP); Noriyuki Fujimori, Suwa (JP); Masatoshi Homan, Hino (JP); Takemitsu Honda, Hino (JP); Hiroshi Suzushima, Nagano (JP); Tatsuya Orihara, Hachioji (JP)

(73) Assignee: Olympus Corporation, Tokyo (JP)

( * ) Notice: Subject to any disclaimer, the term of this patent is extended or adjusted under 35 U.S.C. 154(b) by 1480 days.

(21) Appl. No.: 11/629,649

(22) PCT Filed: Jun. 13, 2005

(86) PCT No.: PCT/JP2005/010792
§ 371 (c)(1),
(2), (4) Date: Feb. 26, 2007

(87) PCT Pub. No.: WO2005/122863
PCT Pub. Date: Dec. 29, 2005

(65) Prior Publication Data
US 2007/0242132 A1 Oct. 18, 2007

(30) Foreign Application Priority Data

Jun. 16, 2004 (JP) .................................. 2004-178563
Jul. 20, 2004 (JP) .................................. 2004-211404

(51) Int. Cl.
*H04N 9/47* (2006.01)
*A61B 1/12* (2006.01)

(52) U.S. Cl. ............ 348/77; 348/65; 600/106; 600/109; 600/155; 600/156

(58) Field of Classification Search .......... 600/101–183; 348/65, 74–77
See application file for complete search history.

(56) References Cited

U.S. PATENT DOCUMENTS

| 5,604,531 A * | 2/1997 | Iddan et al. ..................... 348/76 |
| 6,800,060 B2 * | 10/2004 | Marshall ....................... 600/309 |
| 6,866,626 B2 * | 3/2005 | Long et al. .................... 600/114 |
| 7,343,036 B2 * | 3/2008 | Kleen et al. .................... 382/154 |
| 2003/0092964 A1 | 5/2003 | Kim et al. |
| 2003/0139661 A1 * | 7/2003 | Kimchy et al. .............. 600/407 |
| 2003/0214579 A1 | 11/2003 | Iddan |
| 2004/0030454 A1 | 2/2004 | Kim et al. |
| 2004/0073087 A1 | 4/2004 | Glukhovsky et al. |
| 2006/0173265 A1 * | 8/2006 | Kim et al. .................... 600/407 |
| 2006/0243288 A1 * | 11/2006 | Kim et al. .................... 128/899 |

FOREIGN PATENT DOCUMENTS

| GB | 2 352 636 A | 2/2001 |
| JP | HEI-4-10808 | 3/1992 |
| JP | 2003-19111 | 1/2003 |
| JP | 2003-325438 | 11/2003 |
| WO | WO 01/87377 A2 | 11/2001 |
| WO | WO 02/058531 A2 | 8/2002 |

* cited by examiner

*Primary Examiner* — Brendan Higa
(74) *Attorney, Agent, or Firm* — Scully, Scott, Murphy & Presser, P.C.

(57) ABSTRACT

To achieve a body-insertable apparatus such as a capsule endoscope that moves in a subject at a low speed at which acquisition of in-vivo information is sufficiently possible, the body-insertable apparatus is inserted into the subject and moves in the subject. The body-insertable apparatus includes an in-vivo information acquiring unit that acquires the in-vivo information, an external case member accommodating the in-vivo information acquiring unit, and a moving-speed suppressing unit positioned inside or outside of the external case member to generate a predetermined suppressing force for suppressing the moving speed between an inner wall of a passage route in the subject and the external case member.

15 Claims, 14 Drawing Sheets

BODY-INSERTABLE APPARATUS AND BODY-INSERTABLE APPARATUS SYSTEM

TECHNICAL FIELD

The present invention relates to a body-insertable apparatus inserted into a subject and moving in the subject, and a body-insertable apparatus system using the body-insertable apparatus.

BACKGROUND ART

Recently, in the field of endoscope, a swallowable capsule endoscope has been proposed. The capsule endoscope is provided with an imaging function and a radio communication function. This capsule endoscope has a function of moving in a body cavity, for example, internal organs such as stomach and small intestine with peristalsis thereof, during a period after it is swallowed from a mouth of the subject for observation (examination) until it is naturally discharged from the subject, and imaging intra-subject images, for example, at an interval of 0.5 second with the movement thereof.

While the endoscope is moving in the body cavity, image data imaged in the body by the capsule endoscope is sequentially transmitted to the outside by radio communications, and stored in a memory provided in an external device. If the subject carries a receiving device having the radio communication function and the memory function, the subject swallows the capsule endoscope and then can freely move until the endoscope is discharged. After the capsule endoscope is discharged, a doctor or a nurse can perform diagnosis by displaying the images of the internal organs based on the image data stored in the memory (see, for example, Patent Document 1).

Patent Document 1: Japanese Patent Application Laid-open No. 2003-19111

DISCLOSURE OF INVENTION

Problem to be Solved by the Invention

However, in the conventional capsule endoscope, there is a problem in that in-vivo information such as intra-subject images cannot be acquired sufficiently in a region where passage time of the capsule endoscope is short, as in the esophagus or the like. This problem is explained below.

For example, when the subject maintains a standing posture, the esophagus connects an oral cavity to the stomach in a state extending vertically, and the capsule endoscope inserted into the subject reaches the stomach after having passed the oral cavity, in a state same as free-fall. Taking it into consideration that the whole length of the esophagus is about 30 cm, the capsule endoscope will pass the esophagus within about one second. Therefore, it is not easy to acquire sufficient in-vivo information at the imaging rate of about 0.5 second interval.

On the other hand, for example, when the capsule endoscope has a function of imaging the intra-subject image, it can be considered to acquire sufficient in-vivo information by improving the imaging rate. However, when such a configuration is adopted, a new problem arises such as an increase of power consumption accompanying high-speed operation. Accordingly, at least at the present, it is not desired to improve the imaging rate.

Therefore, a capsule endoscope that can move at an allowable speed even in the esophagus has been desired.

The present invention has been achieved in order to solve the above problems, and it is an object of the present invention to provide a body-insertable apparatus such as the capsule endoscope that moves in the subject at a low speed, at which acquisition of the in-vivo information is sufficiently possible.

Means for Solving Problem

A body-insertable apparatus according to one aspect of the present invention is inserted into the subject and moves in the subject. The body-insertable apparatus also includes an in-vivo information acquiring unit that acquires in-vivo information of the subject, an external case member accommodating the in-vivo information acquiring unit, and a moving-speed suppressing unit positioned inside or outside of the external case member to generate a predetermined suppressing force for suppressing a moving speed in between an inner wall of a passage route in the subject and the external case member.

In the body-insertable apparatus, the moving-speed suppressing unit may include a resistance generator formed on an external surface of the external case member to generate a resistance for blocking movement of the body-insertable apparatus by an interaction generated between a portion of the inner wall of the passage route brought into contact with the body-insertable apparatus and the external case member.

According to this body-insertable apparatus, since the resistance generator that generates a resistance for blocking the movement of the body-insertable apparatus is provided on the external surface of the external case member of the body-insertable apparatus, while the body-insertable apparatus moves with the resistance generator coming in contact with the inner wall of the internal organs in the passage area, the resistance for blocking the movement of the body-insertable apparatus is generated by the resistance generator. Accordingly, the moving speed of the body-insertable apparatus can be reduced.

In the body-insertable apparatus, the resistance generator may be formed of a corrugated member to generate a dynamic friction force as a resistance.

In the body-insertable apparatus, the resistance generator may be formed of a viscous member.

In the body-insertable apparatus, the resistance generator may be formed of a material which has biocompatibility and is gradually decomposed with movement of the body-insertable apparatus inside the subject.

In the body-insertable apparatus, the resistance generator may be formed of a material decomposed by body fluid in the subject.

In the body-insertable apparatus, the resistance generator may be formed to include a muscle contraction agent that contracts at least an inner diameter of the passage route.

In the body-insertable apparatus, the in-vivo information acquiring unit may include an imaging unit, and the external case member includes an imaging window formed of an optically transparent member for allowing light from outside to enter the imaging unit; and a case that is watertightly adhered to the imaging window and accommodates the in-vivo information acquiring unit, and the resistance generator is formed only on the external surface of the case.

In the body-insertable apparatus, the moving-speed suppressing unit may include an adhering mechanism that adheres to an inner wall of the passage route with a predetermined strength, and the external case member accommodates the adhering mechanism.

According to this body-insertable apparatus, since the adhering mechanism adhering at the predetermined strength is provided, by adhering to the inner wall of the passage route at the predetermined strength, the moving speed of the body-insertable apparatus in the subject can be reduced.

In the body-insertable apparatus, the external case member may have a suction-side opening formed in a region of the external case member, and the adhering mechanism makes the body-insertable apparatus adhere to the external case member by sucking external fluid present near the suction-side opening via the suction-side opening.

In the body-insertable apparatus, the external case member may have a discharge-side opening formed in a region other than the region where the suction-side opening is formed, and the adhering mechanism includes a soft tube member that connects the suction-side opening to the discharge-side opening, and a suction operation generator that changes a shape of the soft tube member so that the external fluid is sucked via the suction-side opening and discharged from the discharge-side opening via the soft tube member.

In the body-insertable apparatus, the suction operation generator may include a cam member that rotates about a predetermined shaft to change the shape of the soft tube member so that the soft tube moves peristaltically due to the rotation, and a driving mechanism that supplies rotation torque to the cam member.

In the body-insertable apparatus, the soft tube member may have check valves respectively formed near the suction-side opening and near the discharge-side opening, and the suction operation generator changes the shape of the soft tube so that a volume of a hollow area of the soft tube member between the check valves increases or decreases.

The body-insertable apparatus may further include a pressure detector that detects a pressure of the fluid sucked by the suction-side opening near the suction-side opening of the hollow area of the soft tube member, and a controller that controls driving state of the suction operation generator so that a detection result of the pressure detector is maintained at a predetermined value.

A body-insertable apparatus according to another aspect of the present invention is inserted into a subject for acquiring in-vivo information while moving in the subject, and includes an in-vivo information acquiring unit that acquires the in-vivo information; an external case member accommodating the in-vivo information, acquiring unit, a suction-side opening being formed in a region of the external case member, and a discharge-side opening being formed in other region of the external case member; a soft tube member that connects the suction-side opening to the discharge-side opening; and a displacement operation generator that changes a shape of the soft tube member so that an external fluid present near the suction-side opening is sucked via the suction-side opening and discharged from the discharge-side opening via the soft tube member, and changes at least one of a position and an orientation of the body-insertable apparatus by a reaction force of the suction operation and the discharge operation.

A body-insertable apparatus system according to still another aspect of the present invention includes a body-insertable apparatus inserted into a subject to acquire in-vivo information while moving in the subject and to transmit a radio signal including the in-vivo information acquired, and an external apparatus that receives the radio signal transmitted from the body-insertable apparatus. The body-insertable apparatus includes an in-vivo information acquiring unit that acquires the in-vivo information, an external case member accommodating the in-vivo information acquiring unit, and a moving-speed suppressing unit positioned inside or outside of the external case member to generate a predetermined suppressing force for suppressing a moving speed in between an inner wall of a passage route in the subject and the external case member. The external apparatus includes a receiving circuit that performs receiving processing of the radio signal received via a receiving antenna, and a signal processor that performs predetermined processing with respect to a signal output from the receiving circuit to extract the in-vivo information.

In the body-insertable apparatus system, the moving-speed suppressing unit may include a resistance generator formed on an external surface of the external case member to generate a resistance for blocking movement of the body-insertable apparatus by an interaction generated between a portion of the inner wall of the passage route brought into contact with the body-insertable apparatus and the external case member.

In the body-insertable apparatus system, the moving-speed suppressing unit may include an adhering mechanism that adheres to an inner wall of the passage route with a predetermined strength, and the external case member accommodates the adhering mechanism.

In the body-insertable apparatus system, a suction-side opening may be formed in a region of the external case member and a discharge-side opening is formed in other region of the external case member. The body-insertable apparatus may further include a soft tube member that connects the suction-side opening to the discharge-side opening; a suction operation generator that changes a shape of the soft tube member so that external fluid present near the suction-side opening is sucked via the suction-side opening and discharged from the discharge-side opening via the soft tube member; and a controller that controls driving state of the suction operation generator so as to be a value determined by a predetermined control signal.

In the body-insertable apparatus system, the external device may further include a control signal generator that generates the control signal, and a transmitter that wirelessly transmits the control signal generated by the control signal generator. The body-insertable apparatus may further include a receiver that receives the radio signal transmitted from the transmitter, and a signal processor that extracts the control signal from the radio signal received by the receiver. The controller may perform control based the control signal.

Effect of the Invention

The body-insertable apparatus and the body-insertable apparatus system according to the present invention includes the resistance generator that generates a resistance for blocking the movement of the body-insertable apparatus on the external surface of the external case member of the body-insertable apparatus. Therefore, when the body-insertable apparatus moves while the resistance unit comes in contact with the inner wall of the internal organs in the passage area, the resistance for blocking the movement thereof is generated by the resistance generator. Accordingly, the moving speed of the body-insertable apparatus can be reduced.

The body-insertable apparatus and the body-insertable apparatus system according to the present invention have a configuration of including the adhering mechanism that adheres with a predetermined strength. Accordingly, by adhering to the inner wall of the passage route with a predetermined strength, the moving speed of the body-insertable apparatus in the subject can be reduced.

EXPLANATIONS OF LETTERS OR NUMERALS

Figure 1:
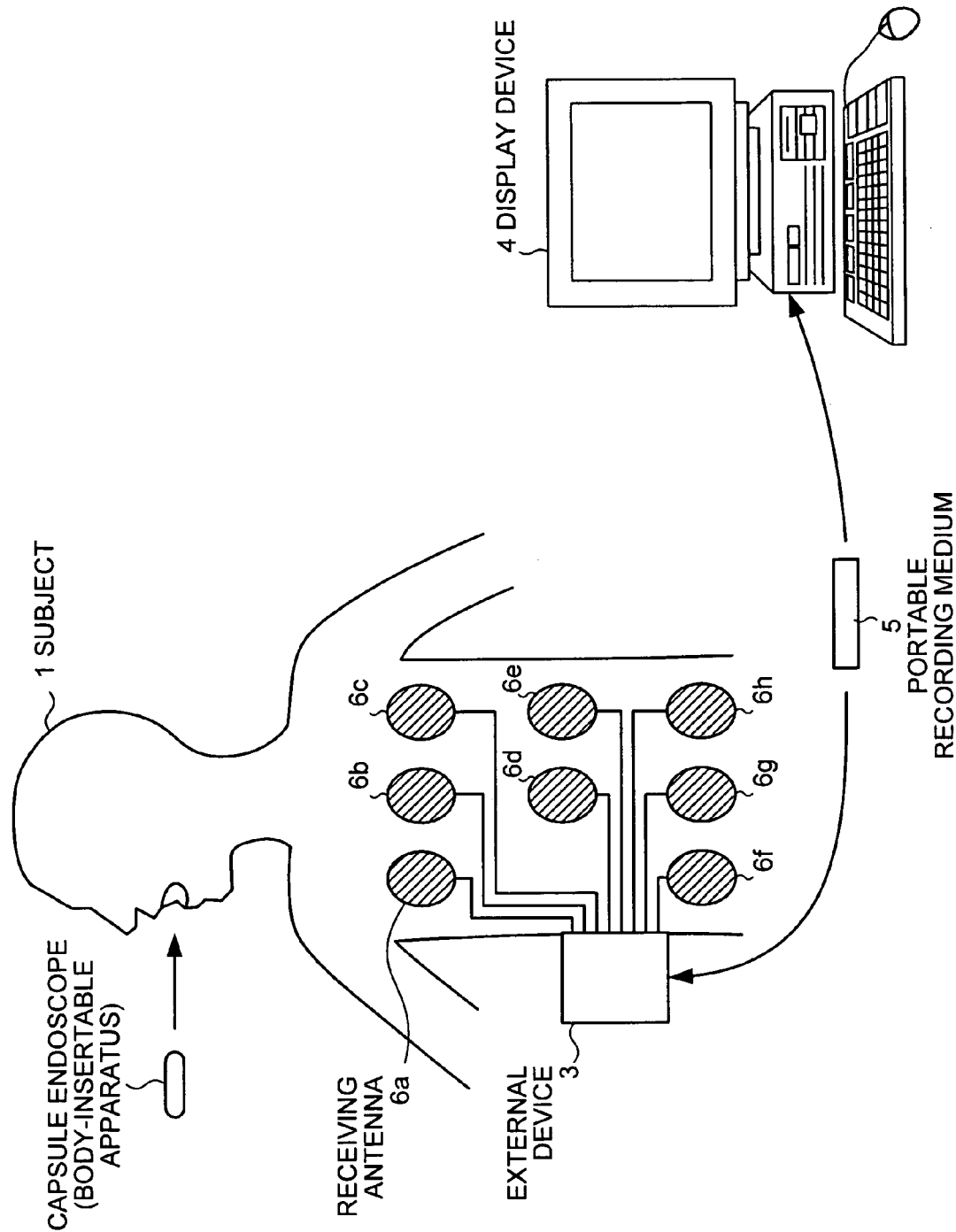
FIG. 1 is a schematic diagram of an entire configuration of a body-insertable apparatus system according to a first embodiment.

1 Subject
2 Capsule endoscope
3 External device
4 Display device
5 Portable recording medium
6a to 6h Receiving antenna
9 Antenna selector
10 Receiving circuit
11 Signal processing unit
12 Control unit
13 Storage unit
14 A/D converter
15 Power supply unit
17 In-vivo information acquiring unit
18 Radio unit
19 Control unit
20 Power supply unit
22 LED
23 LED driving circuit
24 CCD
25 CCD driving circuit
26 Transmitting circuit
27 Transmitting antenna
28 Imaging board
29 External case member
30 Corrugated member
31 Imaging window
32 Case member
33 Digestive organ
34 Contact area
36 Capsule endoscope
37 Viscous member
39 Capsule endoscope
40 Degradable member
51 External device
52 Capsule endoscope
53 Transmitting unit
54 Control unit
54a Selection controller
54b Position calculator
54c Control signal generator
55 Oscillator
56 Superimposing circuit
57 Transmitting circuit
58 Transmitting antenna
61 Receiving unit
62 Signal processing unit
63 Receiving antenna
64 Receiving circuit
65 Control unit
67 Capsule endoscope
68 to 70 Displacing mechanism
71 to 73 Soft tube member
74 to 76 Displacement operation generating unit
77 Control unit
102 Capsule endoscope
119 Adhering mechanism
120 Suction operation generating unit
121 Control unit
131 External case member
132 Suction-side opening
133 Discharge-side opening
134 Soft tube member
135 Rotation shaft
136 Cam member
137 Driving mechanism
138 Pressure detector
139 Constricted region
141 Adhering mechanism
142 Check valve
143 Check valve
144 Soft tube member
145 Suction operation generating unit
146 Guide member
147 Pressing member
148 Driving mechanism
149 Constricted region

BEST MODE(S) FOR CARRYING OUT THE INVENTION

Exemplary embodiments of a body-insertable apparatus and a body-insertable apparatus system according to the present invention will be explained below. Note that the drawings are schematic, and that a relationship between a thickness and a width of each part, and a rate of a thickness of each part are different from actual products. Needless to mention, in some parts, a size relationship and rates are different between the drawings.

First Embodiment

A body-insertable apparatus system according to a first embodiment is explained first. FIG. 1 is a schematic diagram of an entire configuration of the body-insertable apparatus system according to the first embodiment. As shown in FIG. 1, the body-insertable apparatus system according to the first embodiment includes a capsule endoscope 2, which is inserted into a subject 1 and moves along a passage route, an external device 3 that receives a radio signal including in-vivo information transmitted from the capsule endoscope 2, a display device 4 that displays a content of the in-vivo information included in the radio signal received by the external device 3, and a portable recording medium 5 for performing transfer of information between the external device 3 and the display device 4.

The display device 4 displays an intra-subject image and the like imaged by the capsule endoscope 2 and received by the external device 3, and has a configuration like a workstation that displays an image based on data obtained by the portable recording medium 5. Specifically, the display device 4 can have a configuration of directly displaying the image and the like by a CRT display, a liquid crystal display, or the like, or a configuration of outputting the image and the like to another medium like a printer.

The portable recording medium 5 is detachable to the external device 3 and the display device 4, and has a structure capable of outputting and recording information, when it is set in the external device 3 and the display device 4. Specifically, the portable recording medium 5 is set in the external device 3 to store the intra-subject images and a position of a target coordinate axis relative to a reference coordinate axis, while the capsule endoscope 2 is moving in the body cavity of the subject 1. After the capsule endoscope 2 is discharged from the subject 1, the portable recording medium 5 is taken out from the external device 3 and set in the display device 4, and the recorded data is read by the display device 4. Since transfer of data between the external device 3 and the display device 4 is performed by the portable recording medium 5 such as Compact Flash (registered trademark) Memory, the subject 1 can freely move even while the capsule endoscope 2 is moving in the subject 1, different from an instance in which the external device 3 and the display device 4 are connected with each other by wire.

Receiving antennas 6a to 6h are formed, for example, by using a loop antenna. It is desired that the loop antenna is fixed at predetermined positions on a body surface of the subject 1, and a fixing member for fixing the antenna on the body surface is fixed to the loop antenna.

Figure 2:
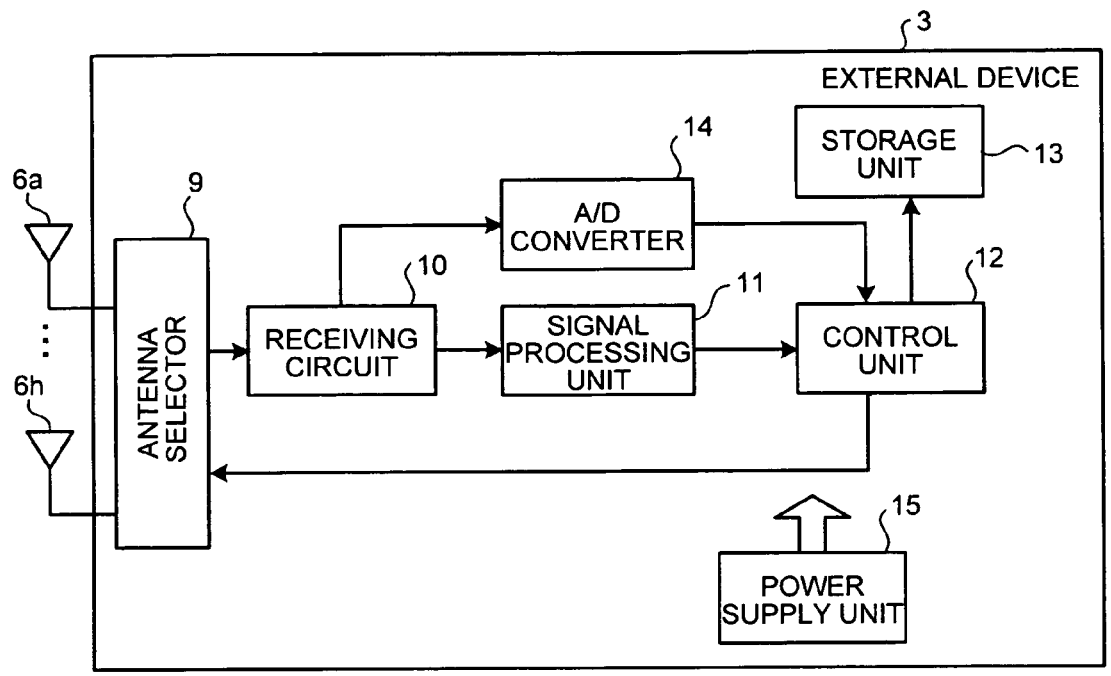
FIG. 2 is a block diagram of a configuration of a receiving apparatus included in the body-insertable apparatus system according to the first embodiment.

The external device 3 performs receiving processing of the radio signal received via any one of the receiving antennas 6a to 6h. FIG. 2 is a block diagram of a configuration of the external device 3. As shown in FIG. 2, the external device 3 includes an antenna selector 9 that selects an antenna suitable for receiving the radio signal from a plurality of receiving antennas 6a to 6h, a receiving circuit 10 that performs processing such as demodulation with respect to the radio signal received via the receiving antenna 6 selected by the antenna selector 9, and a signal processing unit 11 that extracts information relating to a detection magnetic field and the intra-subject image from the radio signal having subjected to the processing. The external device 3 also includes a control unit 12 that performs predetermined control regarding output and the like of the extracted information, a storage unit 13 that stores the extracted information, an A/D converter 14 that A/D converts an analog signal corresponding to strength of the received radio signal, and a power supply unit 15 that supplies driving power for the respective constituent elements.

The antenna selector 9 selects an antenna suitable for receiving the radio signal from a plurality of receiving antennas 6a to 6h. Specifically, the antenna selector 9 selects a predetermined receiving antenna 6 based on the control of the control unit 12, and outputs the radio signal received via the selected receiving antenna 6 to the receiving circuit 10.

The receiving circuit 10 performs predetermined processing such as demodulation relative to the radio signal received via the selected receiving antenna 6. The receiving circuit 10 also outputs the analog signal corresponding to the strength of the radio signal to the A/D converter 14.

The signal processing unit 11 extracts the predetermined information from the signal having subjected to the predetermined processing by the receiving circuit 10. For example, when the radio signal received by the external device 3 is transmitted from electronic equipment having an imaging function, the signal processing unit 11 extracts image data from the signal output from the receiving circuit 10.

The control unit 12 performs overall control including antenna selection by the antenna selector 9. Specifically, the control unit 12 transfers information output from the signal processing unit 11 to the storage unit 13 so as to be stored therein, determines the receiving antenna 6 to be used based on a digital signal (for example, RSSI (Received Signal Strength Indicator)) corresponding to received strength output from the A/D converter 14, and indicates the determined antenna to the antenna selector 9.

The storage unit 13 stores the information extracted by the signal processing unit 11. As a specific configuration of the storage unit 13, the storage unit 13 can include a memory or the like to store the information by itself. However, in the first embodiment, the storage unit 13 has a function of writing the information on the portable recording medium 5.

The capsule endoscope 2 is explained next. The capsule endoscope 2 functions as an example of a body-insertable apparatus, and has functions of obtaining the in-vivo information and transmitting the radio signal including the obtained in-vivo information to the external device 3.

Figure 3:
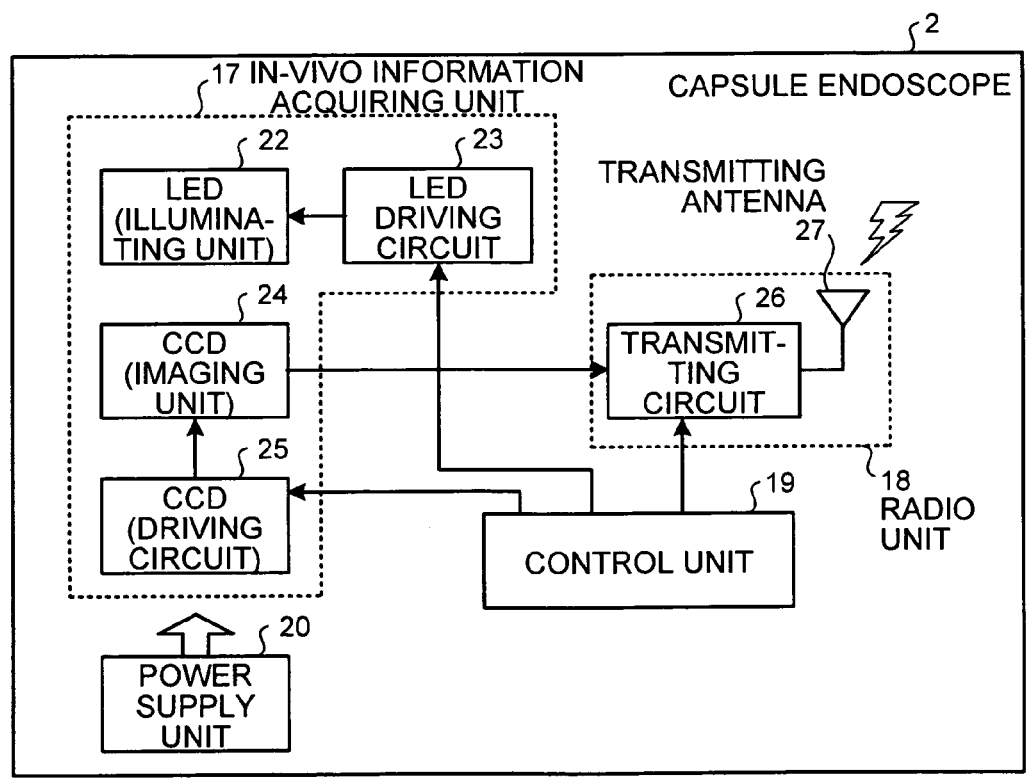
FIG. 3 is a block diagram of an internal configuration of a capsule endoscope included in the body-insertable apparatus system according to the first embodiment.

FIG. 3 is a block diagram schematically showing constituent elements including an intra-subject acquiring unit accommodated in an external case member of the capsule endoscope 2. As shown in FIG. 3, the capsule endoscope 2 includes an in-vivo information acquiring unit 17 that acquires the in-vivo information, a radio unit 18 that generates a radio signal including the in-vivo information and transmits the radio signal to the external device 3, a control unit 19 that controls the driving state of the in-vivo information acquiring unit 17 and the radio unit 18, and a power supply unit 20 that supplies driving power to the constituent elements such as the in-vivo information acquiring unit 17.

The in-vivo information acquiring unit 17 acquires the in-vivo information, and in the first embodiment, for acquiring the intra-subject image. Specifically, the in-vivo information acquiring unit 17 includes a light emitting diode (LED) 22 that outputs an illumination light for illuminating the inside of the subject, an LED driving circuit 23 that controls the driving state of the LED 22, a charge coupled device (CCD) 24 that functions as an imaging unit that images al least one part of an area illuminated by the LED 22, and a CCD driving circuit 25 that controls the driving state of the CCD 24. Intra-subject image data acquired by the CCD 24 is output to the radio unit 18.

The radio unit 18 generates and transmits the radio signal including the in-vivo information output from the in-vivo information acquiring unit 17. Specifically, the radio unit 18 includes a transmitting circuit 26 and a transmitting antenna 27. The radio signal is generated by the transmitting circuit 26, and transmitted via the transmitting antenna 27.

The external part of the capsule endoscope 2 having the constituent elements shown in FIG. 3 accommodated therein is explained. In the first embodiment, the external part has a function of protecting the constituent elements shown in FIG. 3 from outside, and a function of specifying the moving speed of the capsule endoscope 2.

Figure 4:
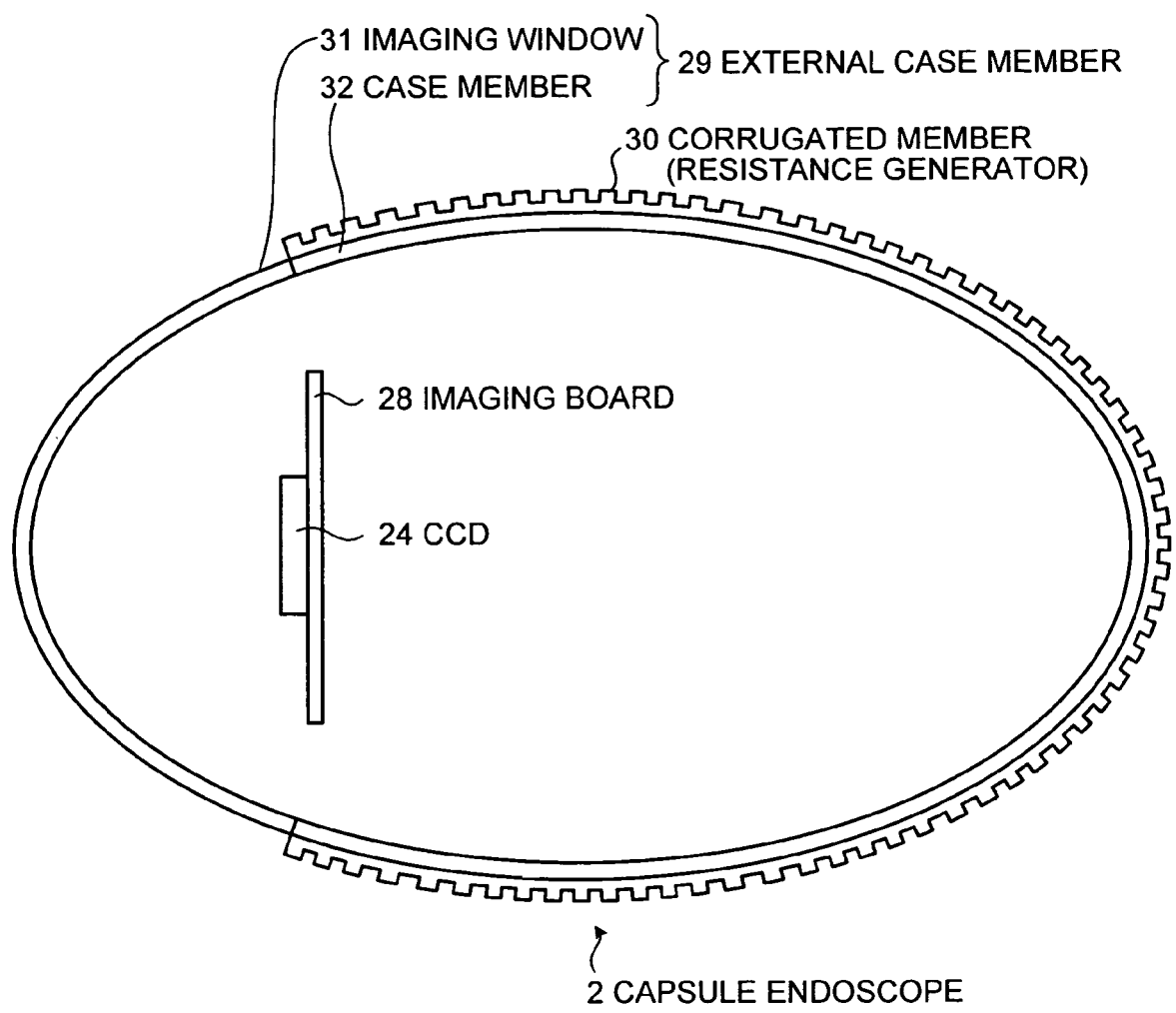
FIG. 4 is a schematic diagram of a physical structure of an external part of the capsule endoscope.

FIG. 4 is a schematic diagram of a cross-sectional structure of the capsule endoscope 2, centering on the structure of the external part. As shown in FIG. 4, the external part of the capsule endoscope 2 includes an external case member 29 and a corrugated member 30 formed on the outside surface of the external case member.

The external case member 29 has a function of protecting the accommodated CCD 24 and the like, by specifying the external shape of the capsule endoscope 2, having a predetermined physical strength, and having a watertight structure as a whole. Specifically, the external case member 29 is formed of an imaging window 31 and a case member 32.

The imaging window 31 allows light from outside of the capsule endoscope 2 to enter the CCD 24 to make it possible to image the intra-subject image by the CCD 24. Specifically, the imaging window 31 is formed of a transparent member or the like having predetermined light transmittance, and arranged in an area corresponding to the CCD 24. In the first embodiment, the imaging window 31 is arranged, as shown in FIG. 4, in an area corresponding to an imaging filed of the CCD 24 formed on an imaging board 28 arranged at a predetermined position in the external case member 29. The case member 32 forms the external case member together with the imaging window 31, and is formed of a member having predetermined physical strength.

The corrugated member 30 functions as an example of a resistance generator. Specifically, the corrugated member 30 is formed on the outside face of the external case member 29, and has a structure of including depressions and protrusions. A height difference between the depressions and protrusions and an individual occupied area ratio of respective depressions and protrusions can be optional if the moving speed described later can be specified. In the first embodiment, it is assumed that the corrugated member 30 has a slightly corrugated structure to form a rough face as the whole corrugated member 30.

It is desired that the corrugated member 30 be formed only on the outside face corresponding to the case member 32, of the outside face of the external case member 29. That is, since scattering of the input light can occur when the corrugated member 30 is formed on the outside face of the imaging window 31, it is necessary to avoid degradation of image quality of the intra-subject image imaged by the CCD 24. To clearly show the structure of the external part, in FIG. 4, the case member 32 and the corrugated member 30 are shown as separate members, however, the case member 32 and the corrugated member 30 can be integrally formed.

Figure 5:
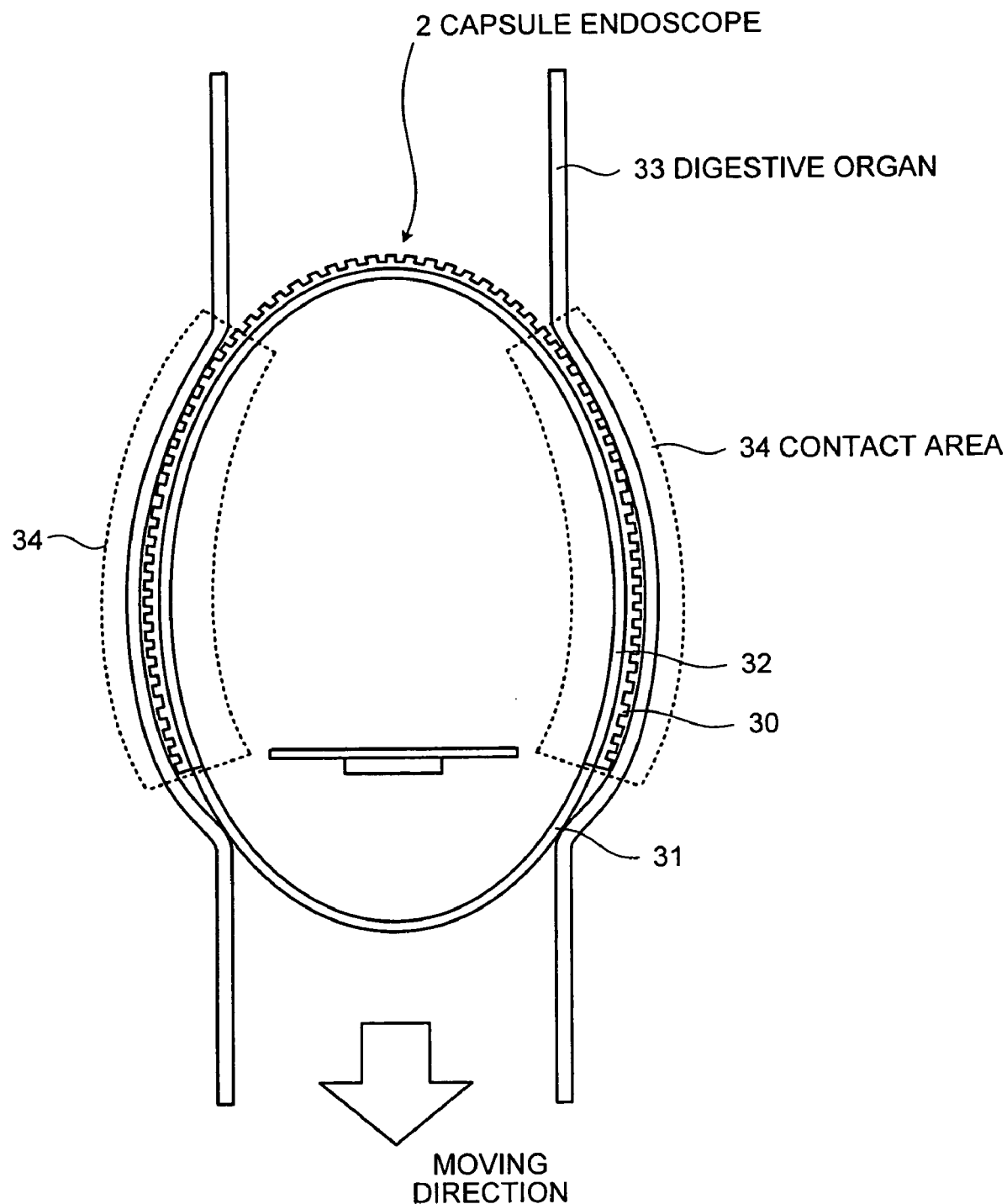
FIG. 5 is a schematic diagram for explaining a function of the external part of the capsule endoscope.

An operation of the corrugated member 30 is explained. FIG. 5 is a schematic diagram of a state in which the capsule endoscope 2 moves inside of the subject 1. The capsule endoscope 2 sequentially passes the digestive organs such as oral cavity, esophagus, stomach, small intestine, and large intestine after it is inserted into the subject 1. Therefore, for example, in the esophagus of the passing route, the capsule endoscope 2 moves, as shown in FIG. 5, while contacting with the inner wall of a tube-like digestive organ 33 in a contact area 34.

In the first embodiment, since the corrugated member 30 is formed on the outside face of the external case member 29, the corrugated member 30 comes in contact with the inner wall of the digestive organ 33, while the capsule endoscope 2 moves, and hence an interaction occurs between the inner wall of the digestive organ 33 and the corrugated member 30. Specifically, a dynamic frictional force acting as a resistance in a direction opposite to the moving direction occurs relative to the capsule endoscope 2, due to the corrugated member 30 coming in contact with the digestive organ 33.

Accordingly, in the first embodiment, the resistance in the direction opposite to the moving direction is supplied in the movement of the capsule endoscope 2 in the subject 1, due to the formation of the corrugated member 30. Since such a resistance disturbs the movement of the capsule endoscope 2, the moving speed of the capsule endoscope 2 in the first embodiment decreases, as compared with a capsule endoscope on which the corrugated member 30 is not formed.

By reducing the moving speed, such an advantage can be obtained that the in-vivo information such as the intra-subject image can be easily acquired in the high-speed passing area such as the esophagus. That is, since the conventional capsule endoscope does not have a function of reducing the moving speed, the conventional capsule endoscope moves at a speed exceeding the capacity of the in-vivo information acquiring unit depending on the passing area, and it is difficult to acquire sufficient in-vivo information.

On the other hand, in the body-insertable apparatus system according to the first embodiment, since the moving speed of the capsule endoscope 2 can be suppressed by forming the corrugated member 30, sufficient time for acquiring the in-vivo information can be ensured even in an area such as the esophagus. Accordingly, in the body-insertable apparatus system according to the first embodiment, the intra-subject images in a sufficient amount for diagnosis and the like can be acquired even for the area such as the esophagus, without increasing the imaging rate of the CCD 24 included in the capsule endoscope 2. Accordingly, a system capable of acquiring reliable in-vivo information can be achieved with low power consumption.

Second Embodiment

The body-insertable apparatus system according to a second embodiment is explained next. In the second embodiment, a viscous member is used as the resistance generator formed on the outside face of the external case member of the capsule endoscope 2.

Figure 6:
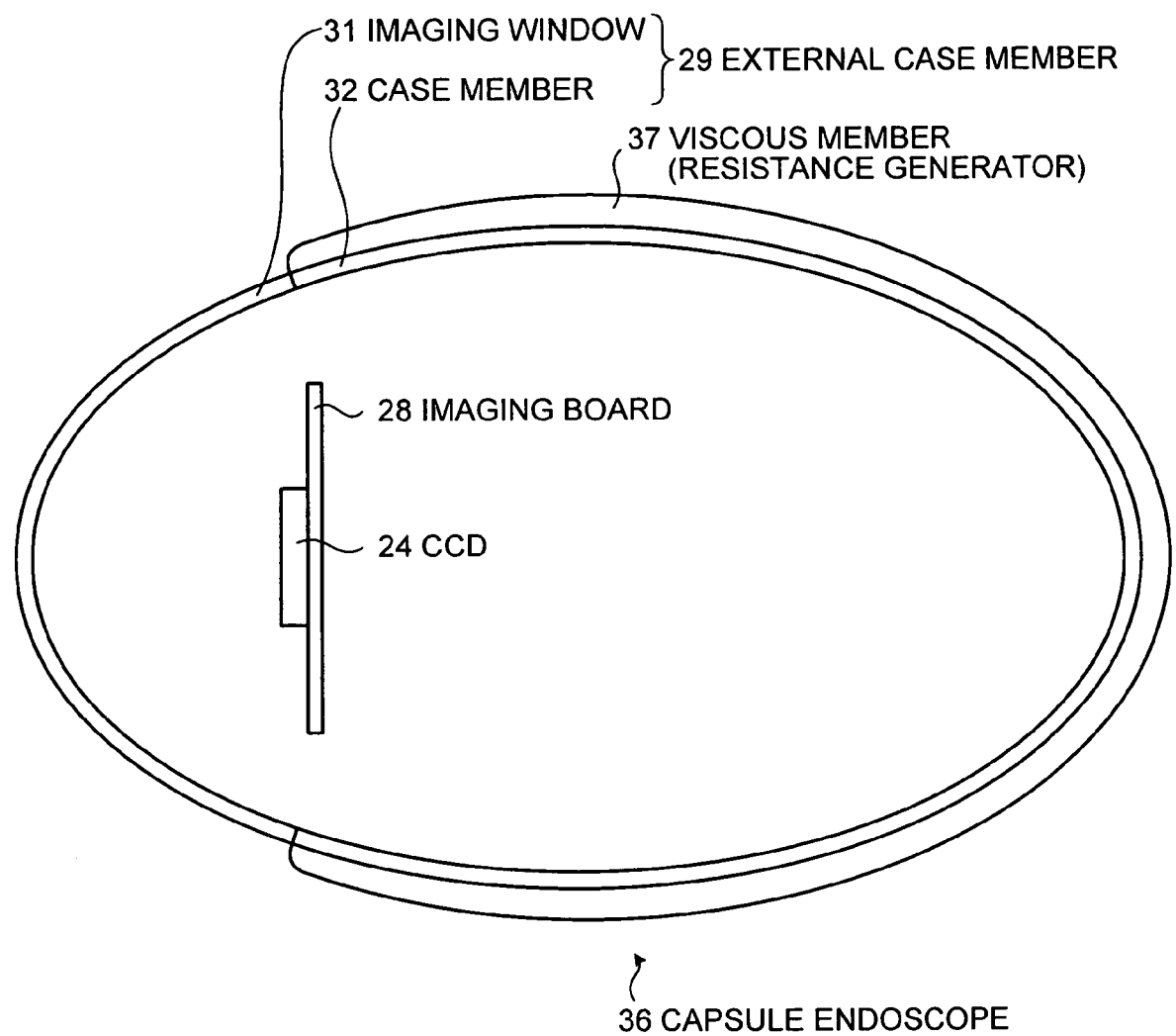
FIG. 6 is a schematic diagram of a physical structure of an external part of a capsule endoscope included in a body-insertable apparatus system according to a second embodiment.

FIG. 6 is a schematic diagram for explaining the external part of a capsule endoscope 36 included in the body-insertable apparatus system according to the second embodiment. Although not shown, the body-insertable apparatus system according to the second embodiment includes the external device 3, the display device 4, and the portable recording medium 5 as in the first embodiment, and the constituent elements shown in FIG. 3 are accommodated in the capsule endoscope 36.

As shown in FIG. 6, in the capsule endoscope 36 in the second embodiment, a viscous member 37 as an example of the resistance generator is arranged on the outside face of the case member 32 forming the external case member 29. The viscous member 37 is formed of, for example, a material having predetermined viscosity such as a gelatinous material, and formed of a material having biocompatibility. Specific materials of the viscous member 37 include an alimentary material, for example, candy material, marshmallow, or oblate. The capsule endoscope 36 in the second embodiment needs only to be such that the viscous member is arranged on the outside face of the external case member at the time of moving in the subject 1. For example, the state shown in FIG. 6 can be obtained by inserting the capsule endoscope having nothing formed on the outside face of the external case member and the viscous member together into the subject 1 at the same time. Further, the viscous member 37 can be formed of a material not having viscosity outside of the subject 1, but generating the viscosity due to an action of the body fluid of the subject 1 or the like when being inserted into the subject 1.

By employing such a configuration, the capsule endoscope 36 moves in the subject 1 in a state with the viscous member 37 coming in contact with the inner wall of the digestive organs corresponding to the passing route. Accordingly, a predetermined shearing stress is applied to a direction parallel to a traveling direction of the capsule endoscope 36 from the inner wall of the digestive organs relative to the viscous member 37, accompanying with the movement of the capsule endoscope 36. Since the viscous member 37 is formed of a material having predetermined viscosity, a shearing resistance occurs as a resistance against the shearing stress, and the resistance is provided relative to the capsule endoscope 36 in a direction opposite to the moving direction. Therefore, in the second embodiment, the shearing resistance generated resulting from the viscous member 37 functions as resistance acting in a direction disturbing the movement of the capsule endoscope 36, and makes the moving speed of the capsule endoscope 36 decrease, like the frictional force in the first embodiment.

An advantage of the body-insertable apparatus system according to the second embodiment is explained below. In the body-insertable apparatus system according to the second embodiment, the moving speed of the capsule endoscope 36 is suppressed due to the resistance in the direction opposite to the moving direction, as in the first embodiment, and sufficient time for acquiring the in-vivo information can be ensured even in an area such as the esophagus.

In the body-insertable apparatus system according to the second embodiment, there is also an advantage in that an influence of the capsule endoscope on the inner wall of the digestive organs can be reduced. That is, in the second embodiment, such a configuration is employed that the viscous member 37 comes in contact with the inner wall of the digestive organs, and the viscous member 37 is normally formed with some flexibility. Therefore, in the capsule endoscope 36 in the second embodiment, the influence on the inner wall is reduced, as compared with the capsule endoscope in which the external case member 29 directly comes in contact with the inner wall of the digestive organs, thereby reducing the burden on the subject 1 in the examination and the like.

Third Embodiment

A body-insertable apparatus system according to a third embodiment is explained next. In the third embodiment, a decomposition material, which is a biocompatible material, and is gradually decomposed with the movement inside the subject, is used as the resistance generator formed on the outside face of the external case member of the capsule endoscope.

Figure 7:
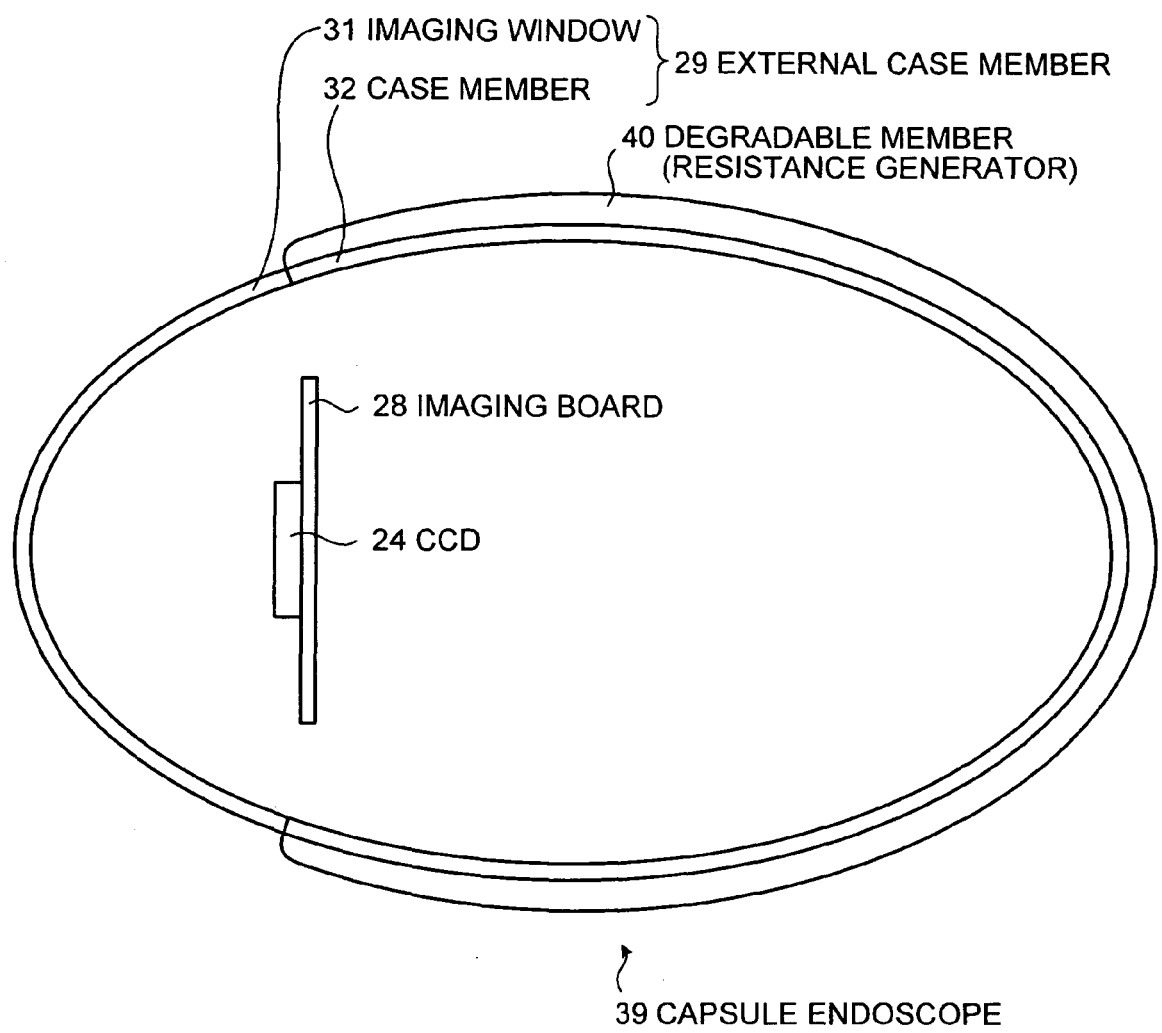
FIG. 7 is a schematic diagram of a physical structure of an external part of a capsule endoscope included in a body-insertable apparatus system according to a third embodiment.

FIG. 7 is a schematic diagram of the external part of a capsule endoscope 39 included in the body-insertable apparatus system according to the third embodiment. As shown in FIG. 7, in the capsule endoscope 39, a degradable member 40 is arranged on the outside face of the case member 32 constituting the external case member 29. Although not shown, the body-insertable apparatus system according to the third embodiment includes the external device 3, the display device 4, and the portable recording medium 5, as in the first embodiment, and the constituent elements shown in FIG. 3 are accommodated in the capsule endoscope 39.

The degradable member 40 is formed of a biocompatible material, which gradually comes off from the capsule endoscope 39 due to decomposition, with the movement of the capsule endoscope 39 inside the subject 1. Specifically, the material forming the degradable member 40 is, for example, a starchy material or the like that is decomposed by the body fluid such as saliva present in the subject 1, and has a function of gradually decomposing due to the action of the body fluid, as it moves in the subject 1. As the degradable member 40, candy material, oblate, and marshmallow indicated as an example of the viscous member in the second embodiment can be also used.

The shape and the like of the degradable member 40 can be the same as in the first and the second embodiments. That is, a frictional force can be generated between the degradable member 40 and the inner wall of the digestive organs by having the corrugated shape as in the first embodiment, or a shearing resistance can be generated by using a viscous material as the material constituting the degradable member. Further, from a reason described later, such a structure can be used that the degradable member 40 is formed thick on the outside face of the case member 32 to improve the degree of adhesion between the inner wall of the digestive organs and the degradable member 40 inside the subject 1, and a resistance in a direction vertical to the contact surface is increased to generate a frictional force between the inner wall of the digestive organs and the degradable member 40.

An advantage of the body-insertable apparatus system according to the third embodiment is explained below. Since the degradable member 40 functions as one example of the resistance generator, as in the first and the second embodiments, an interaction occurs between the inner wall of the digestive organs and the degradable member 40 in the passage area. The moving speed of the capsule endoscope is reduced by generating a resistance in a direction disturbing the movement of the capsule endoscope 39 due to the interaction, thereby enabling the movement of the capsule endoscope 39 at a speed capable of acquiring the in-vivo information sufficiently.

The degradable member 40 in the third embodiment exhibits the function as the resistance generator only when the capsule endoscope 39 moves in a region close to the oral cavity inside the subject 1, for example, the esophagus. In other words, since the degradable member 40 is gradually decomposed with the movement of the capsule endoscope 39, the function as the resistance generator gradually deteriorates with the movement of the capsule endoscope 39. Therefore, the degradable member 40 in the third embodiment functions as the resistance generator only in the digestive organs near the oral cavity such as the esophagus, and the capsule endoscope 39 moves in the stomach, the small intestine, and the like in the same mode as in the conventional capsule endoscope.

Such a characteristic is particularly effective when an insertion object of the capsule endoscope 39 is a subject like a human body, in which the moving speed of the capsule endoscope 39 becomes high immediately after insertion. That is, when the subject 1 is a human body, immediately after the capsule endoscope 39 is inserted via the oral cavity, the capsule endoscope 39 passes through the esophagus, and hence the capsule endoscope 39 moves at a high speed immediately after insertion. On the other hand, when the capsule endoscope 39 passes through the stomach, the small intestine, and the large intestine, the capsule endoscope 39 moves at a low speed sufficiently allowable from a standpoint of acquiring the in-vivo information. Accordingly, in the case of a configuration in which the resistance generator included in the capsule endoscope functions at all times, the capsule endoscope moves at a lower speed than that in the conventional capsule endoscope, at the time of moving through the small intestine and the like.

On the other hand, in the third embodiment, the degradable member 40 functioning as the resistance generator is gradually decomposed with the movement of the capsule endoscope 39. Accordingly, after the capsule endoscope 39 moves in the subject 1 to some extent, the degradable member 40 is separated from the capsule endoscope 39, and the external part of the capsule endoscope 39 changes to the same structure as in the conventional capsule endoscope. Therefore, in the digestive organs away from the oral cavity to some extent, such as the small intestine, the capsule endoscope 39 moves at the same speed as that of the conventional capsule endoscope, without particularly generating the resistance. Therefore, the body-insertable apparatus system according to the third embodiment has an advantage in that an increase of time during which the capsule endoscope 39 stays inside the subject 1 can be suppressed.

Modification

A modification of the body-insertable apparatus system according to the third embodiment is explained next. A degradable member is arranged, as in the third embodiment, on the outside face of the case member 32 of the capsule endoscope included in the body-insertable apparatus system according to the modification, and a muscle contraction agent is mixed in the degradable member.

When such a configuration is adopted, at the time of the degradable member gradually coming off with the movement of the capsule endoscope, the mixed muscle contraction agent is also separated from the capsule endoscope and absorbed by the digestive organs in the passage area. Accordingly, for example, in the esophagus, the muscle contraction agent absorbed via the inner wall of the digestive organs works, such that the inner diameter of the esophagus is narrowed down, or at least enlargement of the inner diameter of the esophagus is suppressed. This means that the inner diameter of the digestive organs as the passage route is narrowed down relative to the outer diameter of the capsule endoscope than in the conventional body-insertable apparatus system, and the size of a normal force acting between the capsule endoscope and the inner wall of the digestive organs increases by the narrowed portion. The resistance such as the frictional force has a characteristic such that it increases corresponding to the value of the normal force. Therefore, by adopting the configuration in which the muscle contraction agent is mixed as in this modification, the resistance acting in a direction disturbing the movement of the capsule endoscope can be increased particularly in the esophagus, thereby giving such an advantage that the moving speed of the capsule endoscope can be further reduced.

The configuration in which the muscle contraction agent is mixed is not necessarily limited to the configuration of the third embodiment. In other words, it is also effective that in the first embodiment, the muscle contraction agent is applied, for example, on the outside face of the corrugated member 30, and in the second embodiment, the muscle contraction agent is applied, for example, on the outside face of the viscous member 37 or the muscle contraction agent is contained inside the viscous member 37.

Fourth Embodiment

A body-insertable apparatus system according to a fourth embodiment is explained next. The fourth embodiment has a configuration in which an adhering unit is used instead of the resistance generator included in the capsule endoscope according to the first to the third embodiments.

Figure 8:
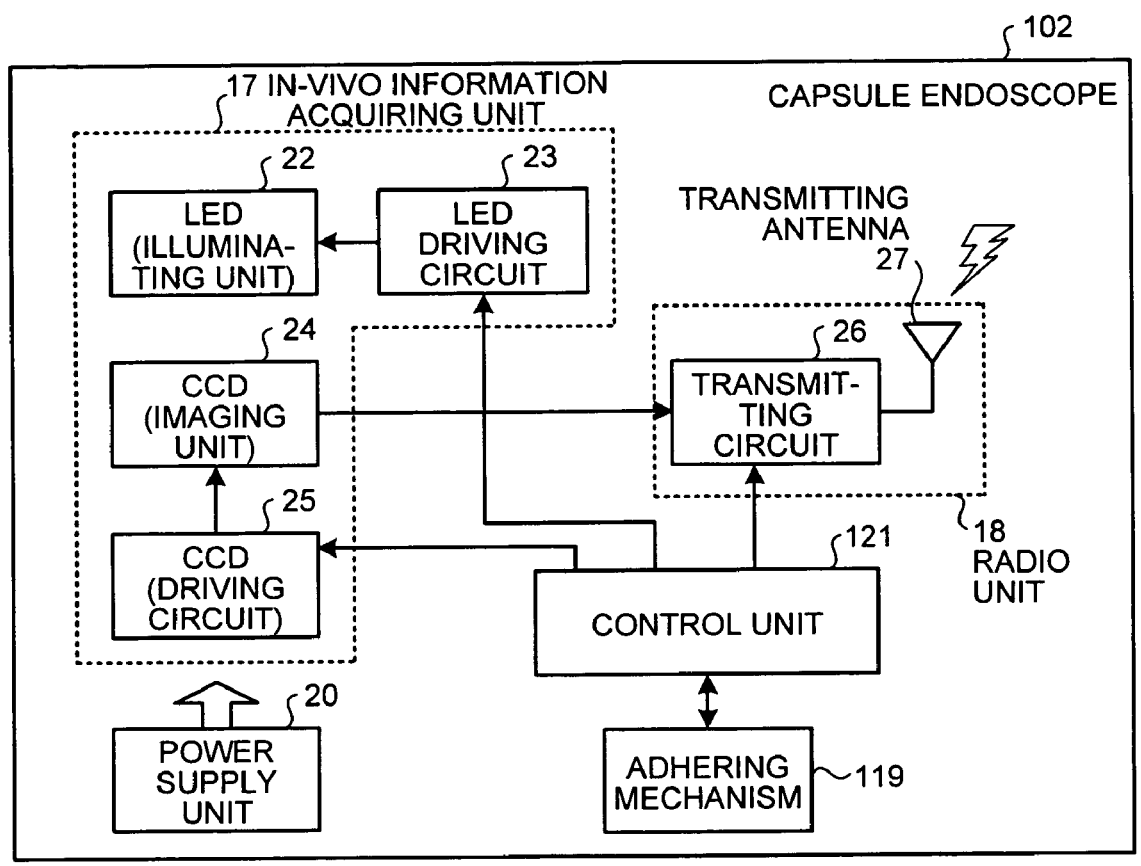
FIG. 8 is a block diagram of a configuration of a capsule endoscope included in a body-insertable apparatus system according to a fourth embodiment.

FIG. 8 is a block diagram schematically showing constituent elements of a capsule endoscope 102 included in the body-insertable apparatus system according to the fourth embodiment. Although not shown, the body-insertable apparatus system according to the fourth embodiment includes the external device 3, the display device 4, and the portable recording medium 5 as in the first embodiment. Constituent elements denoted by like names and reference numerals as in the first embodiment have like structures and actions as in the first embodiment, unless otherwise specified.

As shown in FIG. 8, the capsule endoscope 102 includes a control unit 121 instead of the control unit 19 included in the capsule endoscope 2, and also includes an adhering unit 119. The adhering unit 119 is arranged in a state fixed to the external case member, and has a function of adhering to the inner wall of the digestive organs corresponding to the passage route, to reduce the moving speed of the capsule endoscope 102 by such an adhering function.

Figure 9:
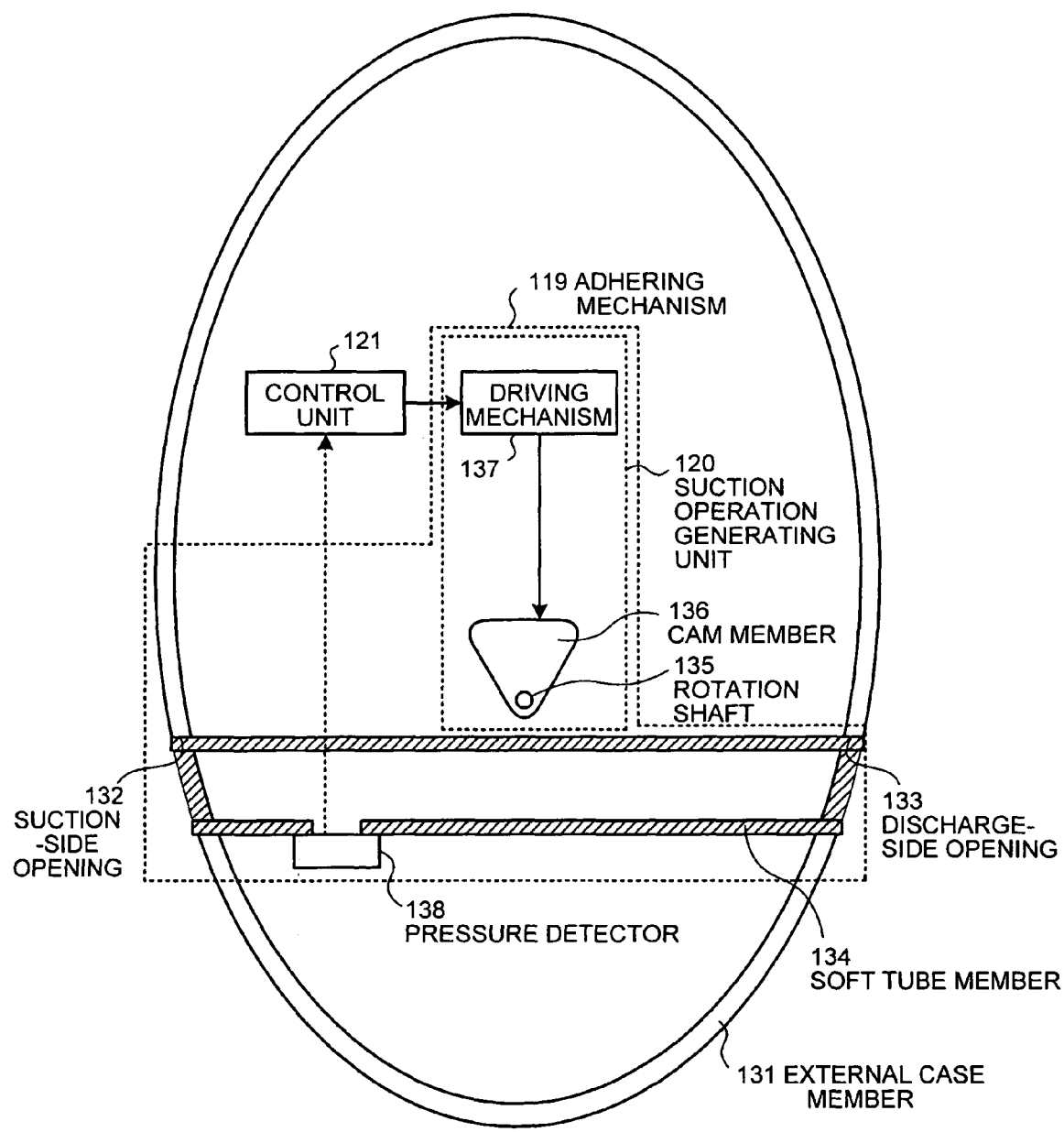
FIG. 9 is a schematic diagram of a structure of an adhering mechanism included in the capsule endoscope.

FIG. 9 is a schematic diagram of a specific structure of the adhering mechanism 119. As shown in FIG. 9, the adhering mechanism 119 includes a soft tube member 134 arranged so as to connect a suction-side opening 132 formed on a partial region of an external case member 131 and a discharge-side opening 133 formed on another region with each other, a suction operation generating unit 120 arranged near the soft tube member 134 to generate suction operation by changing the shape of the soft tube member 134, and a pressure detector 138 that detects a pressure in a predetermined region in a hollow area of the soft tube member 134. The external case member 131 has respective constituent elements shown in FIG. 8 accommodated therein, and is formed of a material having physical strength for protecting the respective constituent elements from outside.

The soft tube member 134 connects the suction-side opening 132 to the discharge-side opening 133, for sucking an external fluid from the suction-side opening 132 due to an action of a cam member 136 as described below, and discharging the external fluid from the discharge-side opening 133. Specifically, the soft tube member 134 has the hollow area for making the suction-side opening 132 and the discharge-side opening 133 continuous to each other, and is formed of a soft material, for example, a rubber material, whose shape easily changes due to the action of the cam member 136.

The suction operation generating unit 120 generates the suction operation by using the soft tube member 134. Specifically, the suction operation generating unit 120 includes the cam member 136 that rotates about a predetermined rotation shaft 135, and a driving mechanism 137 that supplies rotating torque to the cam member 136.

The cam member 136 rotates, using the rotation shaft 135 as an axis, to exert deforming power to the soft tube member 134, so that the shape of the soft tube member 134 is changed. Specifically, the cam member 136 has a configuration such that an outer circumferential portion thereof is eccentric relative to the rotation shaft 135. Since the cam member 136 having such a configuration rotates, the soft tube member 134 causes a shape change corresponding to the rotation angle of the cam member 136.

The driving mechanism 137 supplies the rotating torque to the cam member 136. Specifically, the driving mechanism 137 is formed of, for example, a motor, and has a structure for supplying the generated rotating torque to the cam member 136 via a rotation transmission mechanism such as a predetermined gear or a pulley. The driving mechanism 137 has a configuration such that the driving state is controlled by the control unit 121 as described later.

The pressure detector 138 detects the pressure of the fluid present in the hollow area of the soft tube member 134. More specifically, the pressure detector 138 detects the pressure of the fluid between the suction-side opening 132 and a portion where the shape is changing due to the cam member 136, of the hollow area of the soft tube member 134, preferably, near the suction-side opening 132. The pressure detector 138 is configured so as to output the detected pressure value to the control unit 121.

The control unit 121 is explained next. The control unit 121 has a function of controlling the driving state of the adhering mechanism 119, more specifically, the driving state of the driving mechanism 137 included in the adhering mechanism 119 based on the detection result of the pressure detector 138, in addition to a function of performing predetermined control with respect to the in-vivo information acquiring unit 17 and the radio unit 18.

Specifically, the control unit 121 controls the supplied state of the rotating torque in the driving mechanism 137 so that the detection result of the pressure detector 138 is maintained within a predetermined range. As described later, the size of adhering force of the capsule endoscope 102 by the adhering mechanism 119 corresponds to the degree of suction of the external fluid via the suction-side opening 132, and the degree of suction of the fluid corresponds to the pressure of the fluid near the suction-side opening 132. Therefore, in the fourth embodiment, the control unit 121 controls the driving state of the adhering mechanism 119 corresponding to the detection result of the pressure detector 138, and the size of the adhering force of the capsule endoscope 102 relative to the inner wall of the digestive organs is maintained within a desired range by this control.

In the body-insertable apparatus system according to the fourth embodiment, the adhering operation of the capsule endoscope 102 inserted into the subject 1 is explained. As explained above, in the conventional capsule endoscope, there is a problem in that for example, the moving speed at the time of passing through the esophagus is higher than an acquisition speed of the in-vivo information, thereby making it difficult to acquire the sufficient in-vivo information. In the fourth embodiment, therefore, by providing the adhering mechanism 119, the capsule endoscope 102 adheres to the inner wall of the passage route with predetermined adhering force, thereby reducing the moving speed of the capsule endoscope 102 due to the action of the adhering force.

Figure 10:
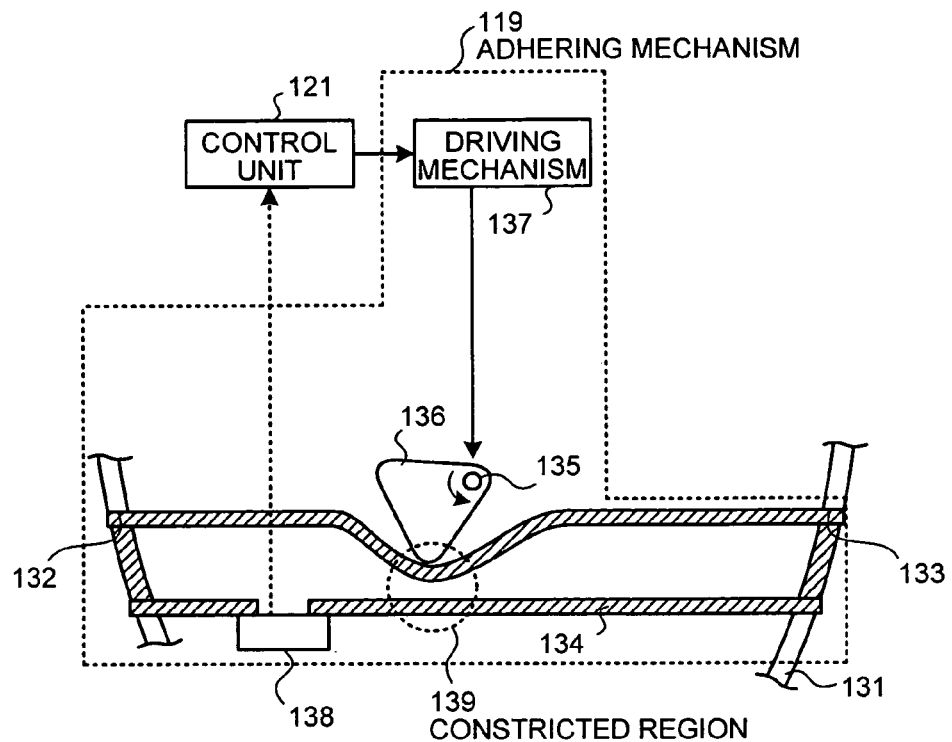
FIG. 10 is a schematic diagram for explaining an operation of the adhering mechanism.
Figure 11:
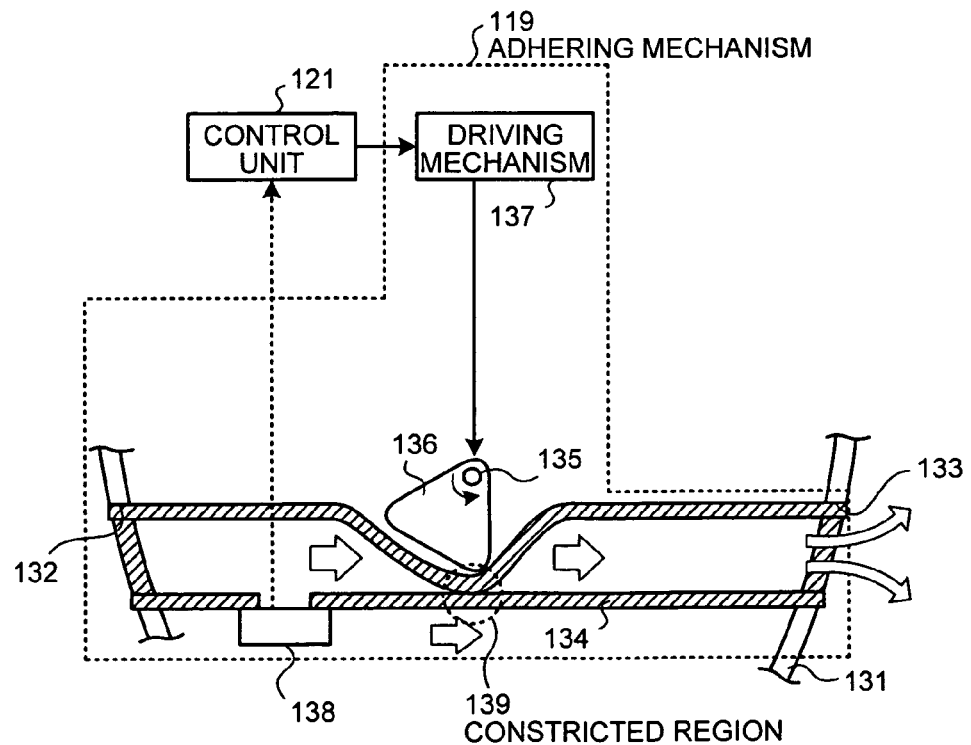
FIG. 11 is a schematic diagram for explaining an operation of the adhering mechanism.

FIGS. 10 and 11 are schematic diagrams for explaining the adhering operation of the adhering mechanism 119. As shown in FIG. 10, the cam member 136 rotates about the rotation shaft 135 in a counterclockwise direction. By this rotation, the outer circumference of the cam member 136, of a portion in which a distance from the rotation shaft 135 becomes equal to or larger than a predetermined value, comes in contact with the soft tube member 134. Due to this contact, a pressing force is applied from the cam member 136 to the soft tube member 134, so that the shape of the portion where the pressing force is applied changes, thereby generating a constricted region 139 in a part of the hollow area of the soft tube member 134.

After the constricted region 139 is formed, the cam member 136 continues to rotate, and the position where the constricted region 139 is formed corresponding to the rotation of the cam member 136 is shifted, as shown in FIG. 11, from the suction-side opening 132 side to the discharge-side opening 133 side. Due to the continuous rotation of the cam member 136, creation and shift of the constricted region 139 is repeated, and hence the soft tube member 134 changes its shape so as to move peristaltically.

Due to such change of the shape of the soft tube member 134, a flow of the fluid from the suction-side opening 132 to the discharge-side opening 133 is generated in the hollow area of the soft tube member 134. In other words, the hollow area receives a thrust pushed out toward the discharge-side opening 133 with the shift of the constricted region 139, and the fluid present in the hollow area moves from the suction-side opening 132 to the discharge-side opening 133. Accompanying such movement of the fluid, an adsorptive power is generated in the region near the suction-side opening 132 of the external area of the capsule endoscope 102. Therefore, the inner wall of the passage route formed by a biomedical tissue of the subject 1 in the area where the capsule endoscope 102 passes adheres to the suction-side opening 132. Since the inner wall adheres to the capsule endoscope 102, the movement of the capsule endoscope 102 is disturbed.

An advantage of the body-insertable apparatus system according to the fourth embodiment is explained next. The body-insertable apparatus system according to the fourth embodiment includes the adhering mechanism 119 in the capsule endoscope 102. Accordingly, due to the adhering force generated by the adhering mechanism 119, the capsule endoscope 102 adheres to the inner wall of the passage route, thereby to disturb the movement of the capsule endoscope 102. Since the moving speed of the capsule endoscope 102 is reduced due to the action of the adhering force, in the fourth embodiment, the moving speed of the capsule endoscope 102 can be reduced to a level capable of acquiring the sufficient in-vivo information by the in-vivo information acquiring unit 17.

In the body-insertable apparatus system according to the fourth embodiment, the control unit 121 controls the driving state of the adhering mechanism 119 based on the detection result of the pressure detector 138. Therefore, the strength of the adhering force generated due to the drive of the adhering mechanism 119 in a region near the suction-side opening 132 of the hollow area of the soft tube member 134 can be set to a value within a certain range. Accordingly, such an ill effect can be prevented that, for example, the strength of the adhering force is too strong and the tissue of the subject 1 is damaged.

In the fourth embodiment, by setting the control range of the adhering force by the control unit 121 to an appropriate value beforehand, the moving speed of the capsule endoscope 102 can be controlled to a desired value. In other words, the moving speed of the capsule endoscope 102 is determined corresponding to a magnitude correlation between a driving force such as gravity provided in a traveling direction of the capsule endoscope 102, and a frictional force occurring between the outside face of the capsule endoscope 102 and the inner wall of the digestive organs determined corresponding to the adhering force of the capsule endoscope 102 relative to the inner wall of the digestive organs as the passage route. Therefore, by appropriately setting the strength range of the adhering force, the moving speed of the capsule endoscope 102 can be appropriately adjusted.

In the fourth embodiment, the configuration is such that the adhering operation of the adhering mechanism 119 is achieved by a shape change of the soft tube member 134 accompanying the rotation of the cam member 136. Therefore, an occupied region of the adhering mechanism 119 can be decreased inside the capsule endoscope 102. That is, by having a configuration in which the cam member 136 rotates about a predetermined rotation shaft 135, a region to be ensured excessively for the operation of the cam member 136 can be reduced. As shown in FIGS. 10 and 11, the soft tube member 134 only has a shape change so as to move peristaltically at the time of generating the adhering force, and a change of the occupied region inside the capsule endoscope 102 does not particularly occur. Therefore, the capsule endoscope 102 in the fourth embodiment has an advantage in that an occupied volume of the adhering mechanism 119 can be reduced.

Modification

A modification of the body-insertable apparatus system according to the fourth embodiment is explained next. In this modification, the soft tube member included in the adhering mechanism has a check valve respectively formed near the suction-side opening 132 and near the discharge-side opening 133.

Figure 12:
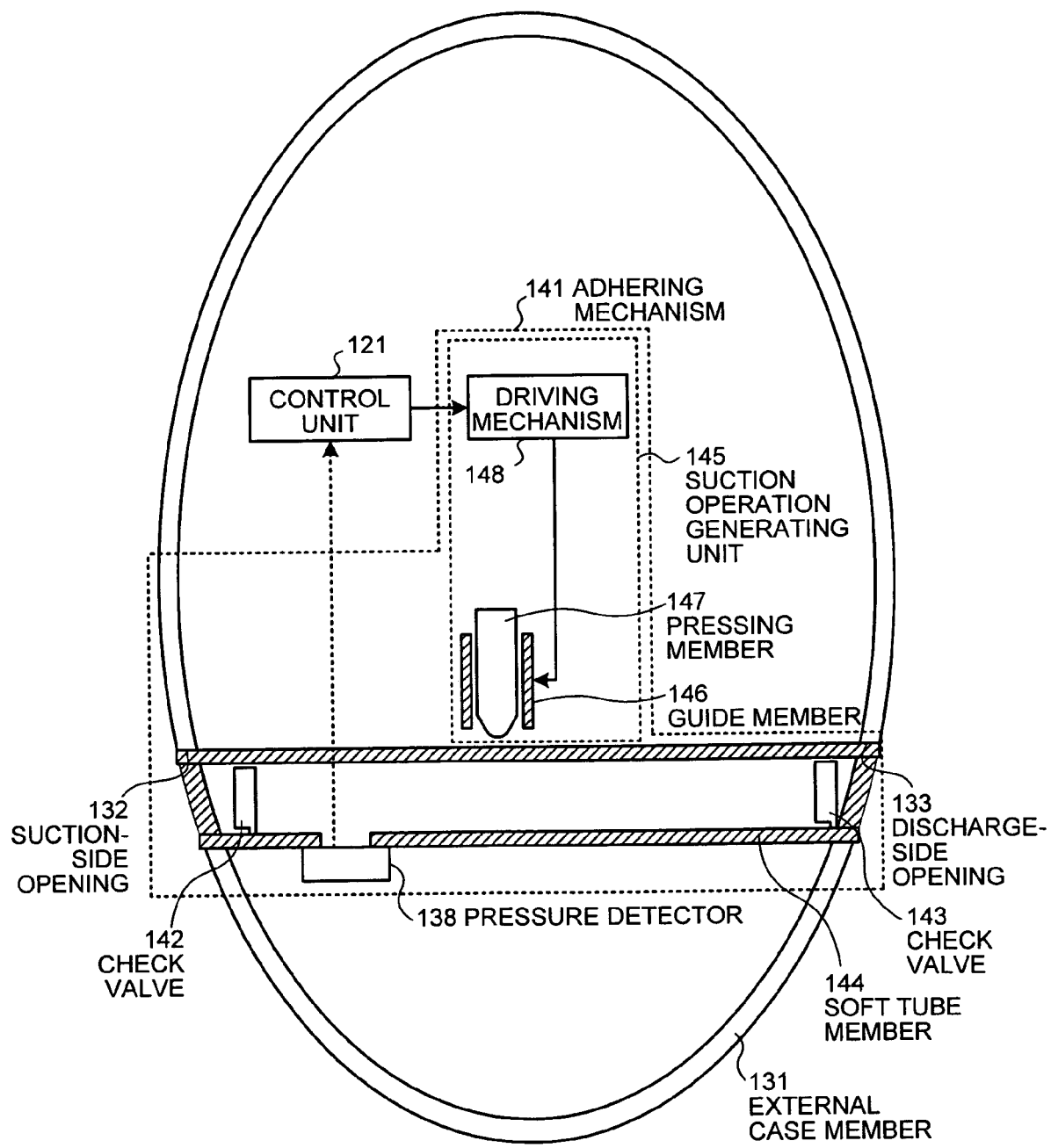
FIG. 12 is a schematic diagram of a structure of the adhering mechanism included in the capsule endoscope according to a modification of the fourth embodiment.

FIG. 12 is a schematic diagram of a structure of an adhering mechanism 141 in the modification. As shown in FIG. 12, the adhering mechanism 141 includes a soft tube member 144 in which a check valve 142 is formed near the suction-side opening 132 and a check valve 143 is formed near the discharge-side opening 133, and a suction operation generating unit 145 that changes the shape of the soft tube member 144 so that a constricted region is formed in a predetermined region.

The check valves 142 and 143 included in the soft tube member 144 have a function of allowing the fluid flowing in a direction from the suction-side opening 132 toward the discharge-side opening 133 (in a rightward direction in FIG. 12) to pass through, and blocking the passage of the fluid flowing in a direction from the discharge-side opening 133 toward the suction-side opening 132. The shape, material, and the like of the soft tube member 144 are the same as those of the soft tube member 134 in the fourth embodiment, except that the check valves 142 and 143 are formed. As a specific structure of the check valves 142 and 143, an optional structure can be employed, so long as the above function is achieved.

The suction operation generating unit 145 forms the constricted region at a predetermined position in the hollow area of the soft tube member 144. Specifically, the suction operation generating unit 145 is formed of a pressing member 147 whose moving direction is determined by a guide member 146, and a driving mechanism 148 that supplies power to the pressing member 147. The pressing member 147 functions so as to apply a thrust to the soft tube member 144 in a direction predetermined by the guide member 146. For example, in an example shown in FIG. 12, the pressing member 147 operates so as to apply the thrust in a longitudinal direction and a perpendicular direction of the soft tube member 144.

Figure 13:
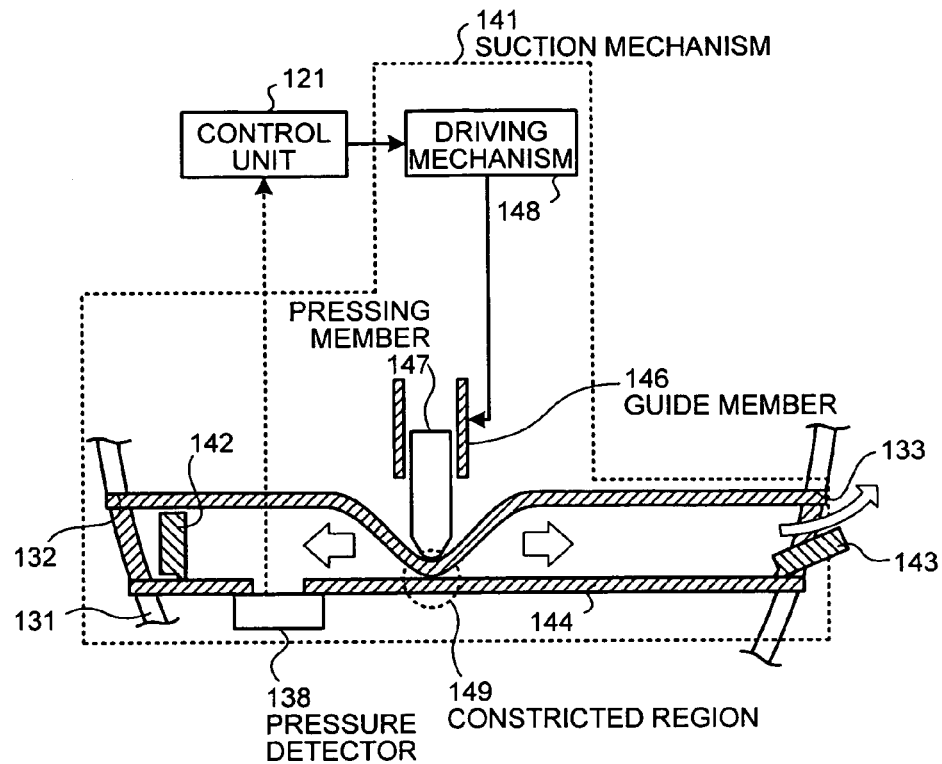
FIG. 13 is a schematic diagram for explaining an operation of the adhering mechanism.
Figure 14:
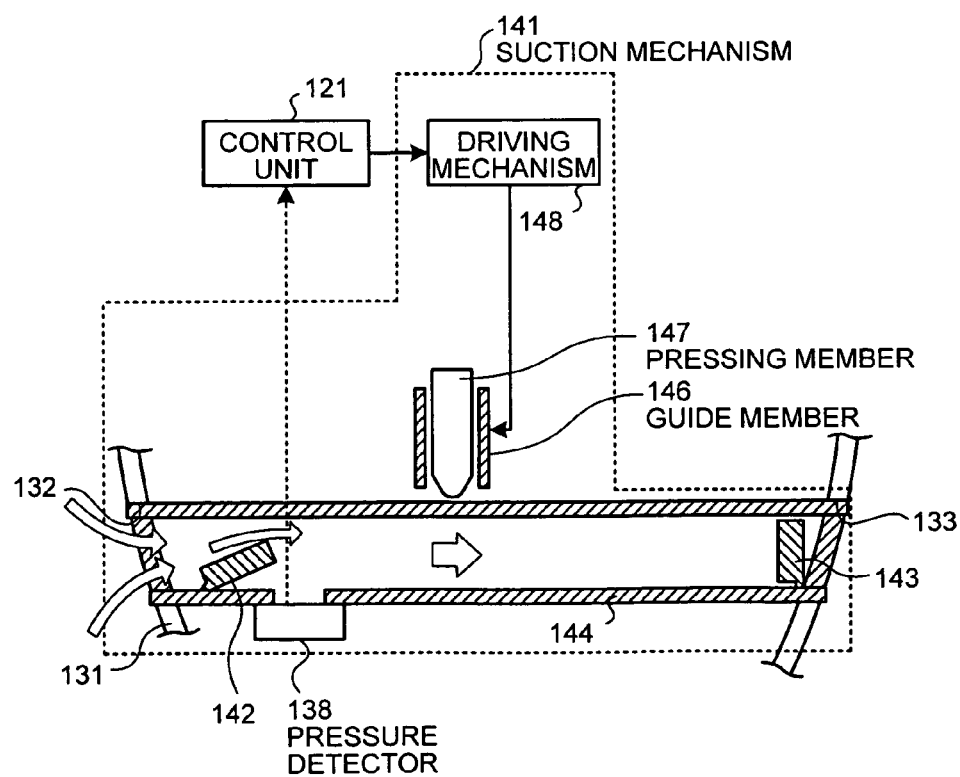
FIG. 14 is a schematic diagram for explaining an operation of the adhering mechanism.

FIGS. 13 and 14 are schematic diagrams for explaining the adhering operation of the adhering mechanism 141 in the modification. Specifically, the adhering mechanism 141 is driven by the driving mechanism 148 based on the control of the control unit 121, and the pressing member 147 applies the thrust to a partial region of the soft tube member 144 based on the power supplied by the driving mechanism 148. The shape of the soft tube member 144 changes due to the application of the thrust, and specifically, a constricted region 149 shown in FIG. 13 is formed.

Accompanying the formation of the constricted region 149, the fluid present in the hollow area of the soft tube member 144 receives a force in a direction away from the constricted region 149. Specifically, as shown by arrows in FIG. 13, the fluid present between the constricted region 149 and the suction-side opening 132 receives a force in a direction toward the suction-side opening 132, and the fluid present between the constricted region 149 and the discharge-side opening 133 receives a force in a direction toward the discharge-side opening 133.

On the other hand, the check valves 142 and 143 have a function of allowing the fluid flowing in a direction from the suction-side opening 132 toward the discharge-side opening 133 to pass through, and blocking the passage of the fluid flowing in an opposite direction. Therefore, the check valve 142 acts to block the passage of the fluid and the check valve 143 acts to allow the passage of the fluid, relative to the flow of the fluid accompanying the formation of the constricted region 149. Accordingly, the fluid present between the constricted region 149 and the discharge-side opening 133 is discharged to the outside of the capsule endoscope 102, while the fluid present between the constricted region 149 and the suction-side opening 132 stays in an original place.

Thereafter, as shown in FIG. 14, the driving mechanism 148 supplies power so as to return the pressing member 147 to an original position, and the soft tube member 144 returns to an original shape in which the constricted region 149 is not present. In the operation shown in FIG. 13, since the fluid between the constricted region 149 and the discharge-side opening 133 is discharged, the amount of the fluid in the hollow area of the soft tube member 144 decreases as compared to the amount before the application of the thrust, due to disappearance of the constricted region 149, and fluid present outside of the capsule endoscope 102 flows in via the suction-side opening 132. As a reaction to the inflow pressure, an adhering force that makes the capsule endoscope 102 adhere to the inner wall of the passage route is generated, and the capsule endoscope 102 adheres to the inner wall of the passage route.

By having such an adhering mechanism 141, the moving speed of the capsule endoscope 102 can be controlled as in the fourth embodiment. Also in the modification, since the adhering force is generated by a simple mechanism, the simple and small adhering mechanism 141 can be achieved.

Fifth Embodiment

A body-insertable apparatus system according to a fifth embodiment is explained. In the body-insertable apparatus system according to the fifth embodiment, an external device transmits a radio signal including a predetermined control signal to the capsule endoscope, and the capsule endoscope includes a predetermined receiving function, and controls the adhering operation based on the control signal included in the radio signal received by the receiving function.

Figure 15:
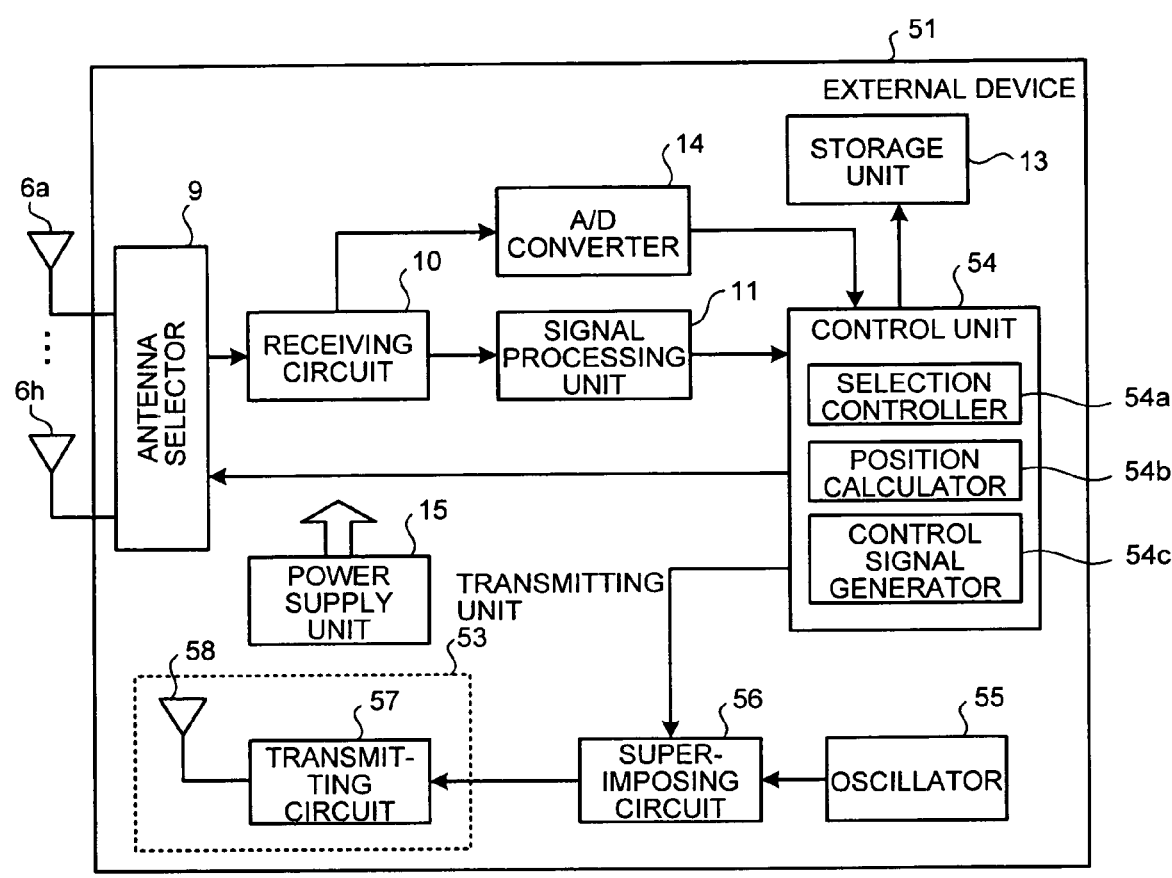
FIG. 15 is a schematic diagram of a configuration of an external device included in a body-insertable apparatus system according to a fifth embodiment.
Figure 16:
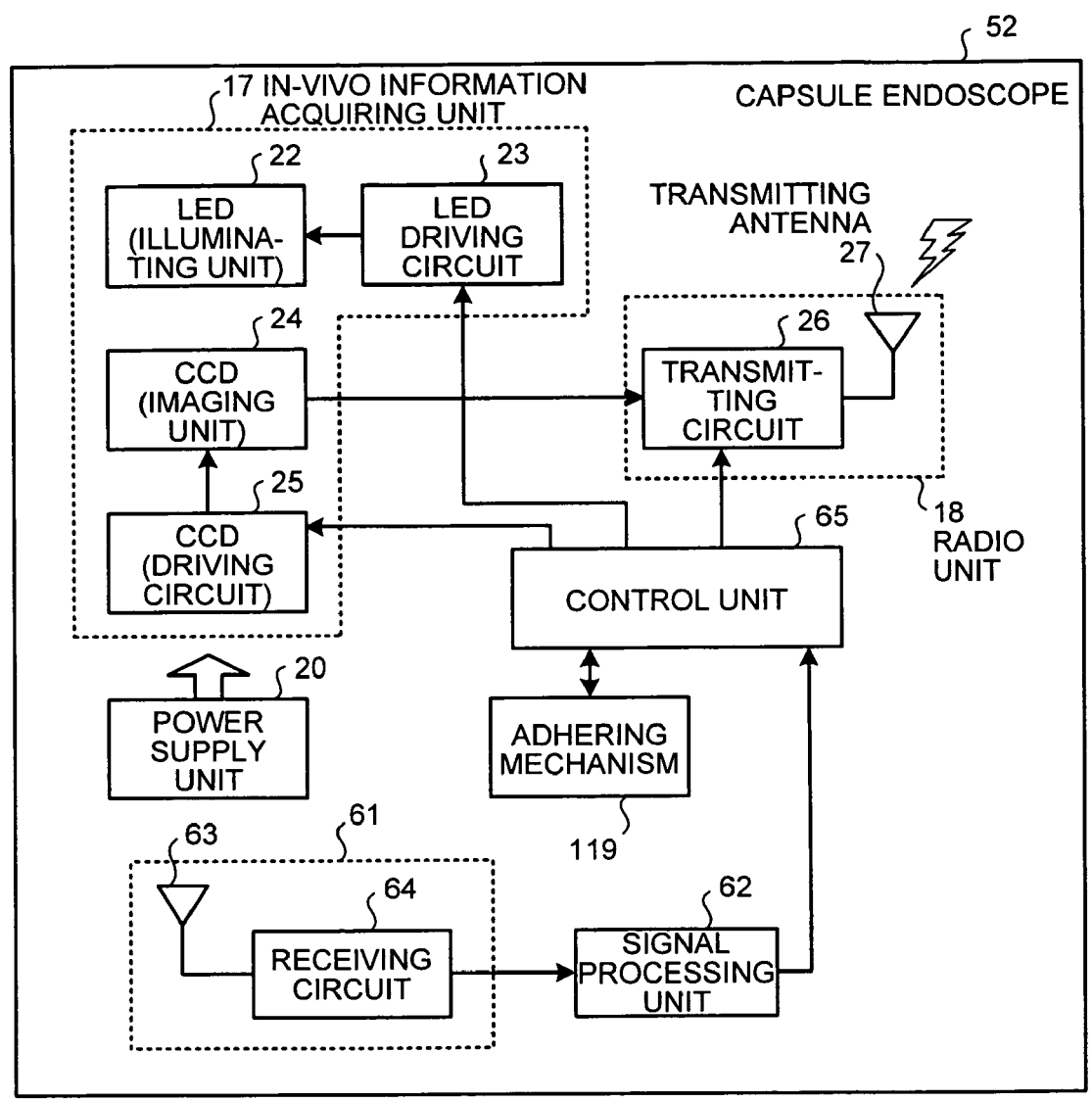
FIG. 16 is a schematic diagram of a configuration of the capsule endoscope included in the body-insertable apparatus system according to the fifth embodiment.

FIG. 15 is a block diagram of a configuration of an external device 51 included in the body-insertable apparatus system according to the fifth embodiment, and FIG. 16 is a block diagram of a configuration of a capsule endoscope 52 included in the body-insertable apparatus system. Although not shown, the body-insertable apparatus system according to the fifth embodiment includes the display device 4 and the portable recording medium 5 as in the fourth embodiment, and constituent elements denoted by like names or reference numerals as in the fourth embodiment have like structures and actions as in the fourth embodiment, unless otherwise specified.

As shown in FIG. 15, the external device 51 newly includes a transmitting unit 53, and has a function of transmitting a radio signal including a predetermined control signal from the transmitting unit 53. Specifically, the external device 51 includes a control unit 54 having a function of generating the control signal, an oscillator 55 that specifies the frequency of the radio signal, a superimposing circuit 56 that superimposes the control signal generated by the control unit 54 on a signal output from the oscillator, a transmitting circuit 57 constituting the transmitting unit 53, and a transmitting antenna 58.

The control unit 54 includes a selection controller 54a that controls antenna selection as in the control unit 121 in the fourth embodiment, a position calculator 54b that calculates the position of the capsule endoscope 52 based on received strength of the radio signal received via a plurality of receiving antennas 6, and a control signal generator 54c that generates a control signal based on the position of the capsule endoscope 52 calculated by the position calculator 54b.

The position calculator 54b calculates the position of the capsule endoscope 52 in the subject 1. As explained in the first embodiment, the external device 51 has a mechanism for calculating the received strength of the radio signal in each of the receiving antennas 6a to 6h by the action of the receiving circuit 10 and the A/D converter 14. In the first embodiment, only the antenna selection is performed by using the received strength. However, in the fifth embodiment, the position of the capsule endoscope 52 is calculated based on the value of the received strength. That is, the radio signal transmitted from the capsule endoscope 52 has a characteristic such that the radio signal attenuates corresponding to a distance from the capsule endoscope 52, and hence the received strength in the receiving antenna reflects the distance from the capsule endoscope 52.

Therefore, the position calculator 54b ascertains the positions of the respective receiving antennas 6a to 6h on the subject 1 beforehand, and calculates distances between a plurality of, for example, three receiving antennas 6 and the capsule endoscope 52 based on the received strength of the radio signal. The position calculator 54b then performs predetermined calculation by using the calculated distances and the positions of the receiving antennas 6 to calculate the position of the capsule endoscope 52.

The control signal generator 54c has a function of generating a control signal for controlling the operation of the adhering mechanism 119 included in the capsule endoscope 52. The control signal generator 54c generates the control signal based on the calculation result of the position calculator 54b, in the fifth embodiment, thereby to generate a different control signal corresponding to the position of the capsule endoscope 52. The control signal generated by the control signal generator 54c is wirelessly transmitted by the transmitting unit 53.

The capsule endoscope 52 is explained next. As shown in FIG. 16, the capsule endoscope 52 includes a receiving unit 61 that receives the radio signal transmitted by the transmitting unit 53 included in the external device 51, a signal processing unit 62 that extracts the control signal from the radio signal received by the receiving unit 61, and a control unit 65 that performs predetermined control. The receiving unit 61 is formed of a receiving antenna 63 and a receiving circuit 64.

The control unit 65 has a function of controlling the drive of the adhering mechanism 119 corresponding to the content of the control signal input from the signal processing unit 62, in addition to the function of the control unit 121 in the fourth embodiment. The control signal includes, for example, information relating to on/off of the adhering mechanism 119 and the range of pressure of the fluid to be maintained, and the control unit 65 has a function of performing control based on the content of the control signal including such information.

An advantage of the body-insertable apparatus system according to the fifth embodiment is explained. The capsule endoscope 52 included in the body-insertable apparatus system according to the fifth embodiment has a configuration including the adhering mechanism 119 as in the fourth embodiment. Therefore, the same advantage as that of the fourth embodiment, such that the moving speed of the capsule endoscope 52 can be controlled, can be obtained.

Further, in the fifth embodiment, the control unit 54 includes the control signal generator 54c, thereby providing an advantage in that the operation of the adhering mechanism 119 can be controlled from outside. For example, in the fifth embodiment, the control signal generator 54c has a function of generating the control signal based on the calculation result of the position calculator 54b. By having such a configuration, the capsule endoscope 52 can be moved at a speed capable of acquiring sufficient and efficient in-vivo information.

In other words, the capsule endoscope 52 does not always move at a constant speed. For example, the capsule endoscope 52 moves at a high speed at the time of passing through the esophagus, while it moves at a speed sufficiently capable of acquiring the in-vivo information without using the action of the adhering mechanism at the time of passing through the small intestine and the large intestine. Accordingly, in the fifth embodiment, it can be considered that while the capsule endoscope 52 passes through the esophagus, the control signal generator 54c generates a control signal instructing the adhering mechanism 119 to adhere with high strength, and while the capsule endoscope 52 passes through the small intestine and the large intestine, the control signal generator 54c generates a control signal instructing suspension of the drive of the adhering mechanism 119. By performing such control based on the control signal, the body-insertable apparatus system according to the fifth embodiment can appropriately control the driving state of the adhering mechanism 119 corresponding to the position inside the subject 1. As a result, such an ill effect can be prevented that the moving speed, for example, in the small intestine considerably decreases, thereby enabling efficient acquisition of the in-vivo information.

Sixth Embodiment

A body-insertable apparatus system according to a sixth embodiment is explained next. In the sixth embodiment, a capsule endoscope that can positively change the position inside the subject 1 by applying the adhering mechanism explained in the fourth and the fifth embodiments is provided.

Figure 17:
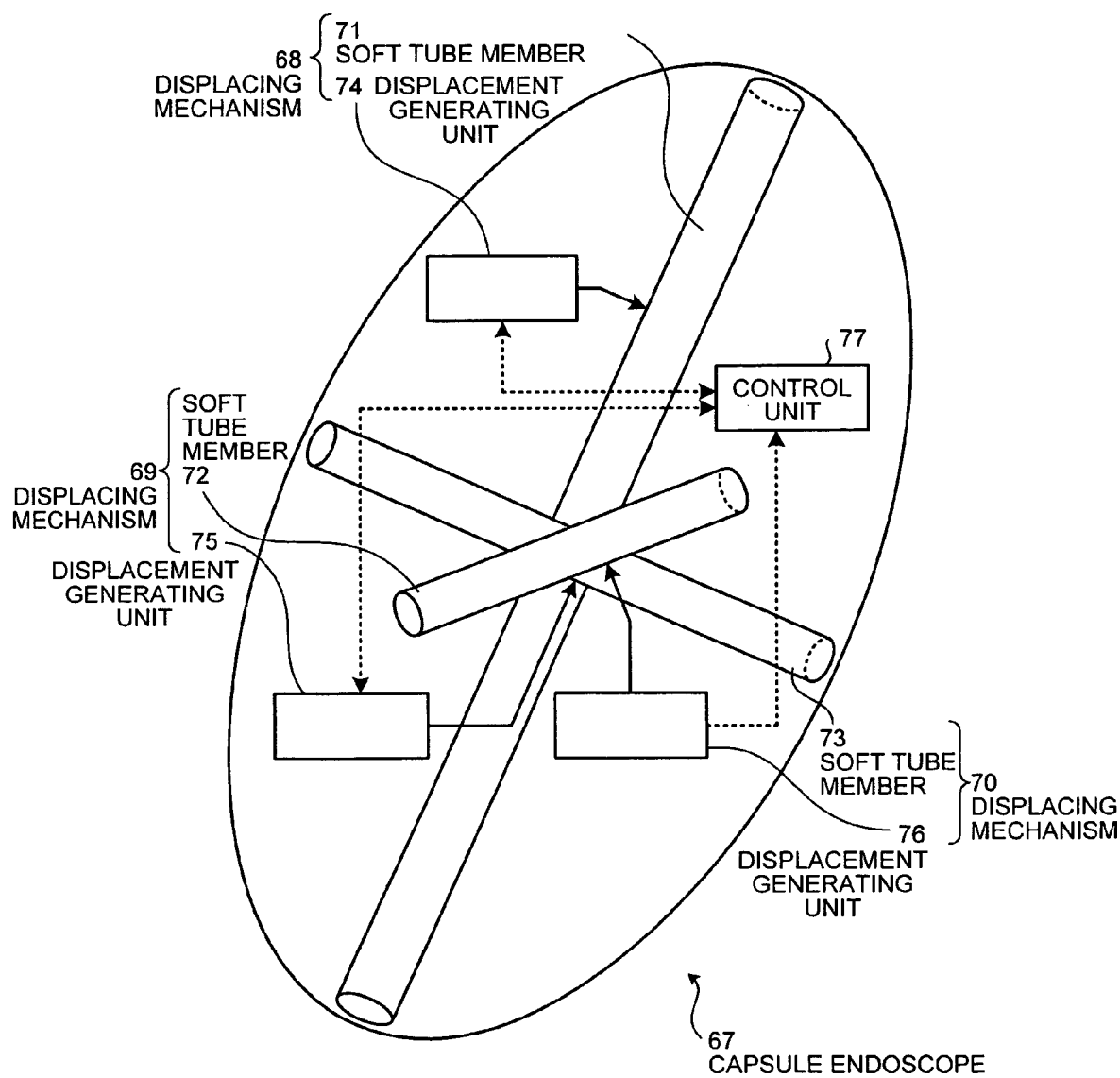
FIG. 17 is a schematic diagram of a configuration of a capsule endoscope included in a body-insertable apparatus system according to a sixth embodiment.

FIG. 17 is a schematic diagram of a configuration of displacing mechanisms 68 to 70 included in a capsule endoscope 67 constituting the body-insertable apparatus system in the sixth embodiment. Although not shown, the body-insertable apparatus system according to the sixth embodiment includes the external device 3, the display device 4, and the portable recording medium 5 as in the fourth embodiment. Further, a mechanism shown in FIG. 8 excluding the adhering mechanism 119 and the control unit 121 is included in the capsule endoscope 67.

As shown in FIG. 17, the displacing mechanism 68 to 70 respectively have a configuration including a soft tube member 71 to 73 extending in a direction different from each other, for example, orthogonal to each other, and a displacement operation generating unit 74 to 76 that changes the shape of the soft tube member 71. The displacement operation generating units 74 to 76 have a function of changing the shape of the soft tube member 71 based on the control of the control unit 77.

The soft tube members 71 to 73 are formed of the same material and in the same shape as that of the soft tube member 34, for example, in the fourth embodiment. That is, the soft tube members 71 to 73 are formed so as to connect the suction-side opening and the discharge-side opening formed on the outside face of the capsule endoscope 67, and have a configuration such that the shape of the soft tube members 71 to 73 changes so as to move peristaltically due to the thrust provided by the displacement operation generating units 74 to 76.

The displacement operation generating units 74 to 76 have the same configuration as that of the suction operation generating unit 120 in the fourth embodiment. That is, the displacement operation generating units 74 to 76 respectively include the cam member that rotates about a predetermined rotation shaft and the driving mechanism that supplies rotation torque of a size according to the control of the control unit 77 to the cam member.

In the sixth embodiment, the position of the capsule endoscope 67 is changed by using not only the fluid flow at the suction-side opening but also at the discharge-side opening. That is, the external fluid sucked via the suction-side opening passes through the hollow area of the soft tube member, and is discharged to the outside via the discharge-side opening. At the time of discharging operation, the capsule endoscope 67 receives a reaction force in a direction opposite to the discharge direction from the discharged fluid. In the sixth embodiment, therefore, the position of the capsule endoscope 67 is changed by using a force corresponding to the adhering force generated near the suction-side opening and the reaction force received from the discharged fluid as the driving force.

When the soft tube members 71 to 73 are arranged so as to pass a barycentric position of the capsule endoscope 67, the capsule endoscope 67 translates in a direction parallel to an extending direction of the soft tube members 71 to 73. It is desired to adopt such a configuration from a standpoint of enabling the movement of the capsule endoscope 67. However, on the other hand, the orientation of the capsule endoscope 67 can be changed by setting the arranged position of the soft tube member 71 to an area not passing the barycentric position of the capsule endoscope 67. In other words, when the moving direction of the external fluid and a direction connecting the opening and the barycentric position of the capsule endoscope 67 are not parallel to each other at the suction-side opening or the discharge-side opening corresponding to the end of the soft tube member 71 or the like, the capsule endoscope 67 rotates corresponding to an angle between these. By contriving the arrangement of the soft tube member 71 or the like so as to perform such a rotating operation, a capsule endoscope capable of controlling its orientation can be achieved.

INDUSTRIAL APPLICABILITY

As described above, the body-insertable apparatus and the body-insertable apparatus system according to the present invention are useful for a body-insertable apparatus system including a body-insertable apparatus that is inserted into a subject, acquires in-vivo information while moving in the subject, and transmits a radio signal including the acquired in-vivo information, and an external device that receives the radio signal transmitted from the body-insertable apparatus, and is particularly suitable for a body-insertable apparatus system using a capsule endoscope as the body-insertable apparatus.

The invention claimed is:

1. A body-insertable apparatus inserted into a subject to move in the subject, comprising:
   an in-vivo information acquiring unit acquiring in-vivo information of the subject;
   an external case member accommodating the in-vivo information acquiring unit; and
   a moving-speed suppressing unit positioned inside or outside of the external case member to generate a predetermined suppressing force for suppressing a moving speed in between an inner wall of a passage route in the subject and the body-insertable apparatus,
   wherein the moving-speed suppressing unit includes an adhering mechanism that adheres to an inner wall of the passage route with a predetermined strength by sucking external fluid present near a suction-side opening via the suction-side opening, the adhering mechanism comprising a soft tube member that connects the suction-side opening to a discharge-side opening and a suction operation generator that changes a shape of the soft tube member so that the external fluid is sucked via the suction-side opening and discharged from the discharge-side opening via the soft tube member
   wherein the external case member accommodates the adhering mechanism, has the suction-side opening formed in a region of the external case member and the external case member has the discharge-side opening formed in a region other than the region where the suction-side opening is formed.

2. The body-insertable apparatus according to claim 1, wherein the moving-speed suppressing unit includes a resistance generator formed on an external surface of the external case member to generate a resistance for blocking movement of the body-insertable apparatus by an interaction generated between a portion of the inner wall of the passage route brought into contact with the body-insertable apparatus and the body-insertable apparatus.

3. The body-insertable apparatus according to claim 2, wherein the resistance generator is formed of a corrugated member to generate a dynamic friction force as a resistance.

4. The body-insertable apparatus according to claim 2, wherein the resistance generator is formed of a viscous member.

5. The body-insertable apparatus according to claim 2, wherein the resistance generator is formed of a material which has biocompatibility and is gradually decomposed with movement of the body-insertable apparatus inside the subject.

6. The body-insertable apparatus according to claim 5, wherein the resistance generator is formed of a material decomposed by body fluid in the subject.

7. The body-insertable apparatus according to claim 2, wherein the resistance generator is formed to include a muscle contraction agent that contracts at least an inner diameter of the passage route.

8. The body-insertable apparatus according to claim 2, wherein the in-vivo information acquiring unit includes an imaging unit, and
   the external case member includes
      an imaging window formed of an optically transparent member for allowing light from outside to enter the imaging unit; and a case that is watertightly adhered to the imaging window and accommodates the in-vivo information acquiring unit, and the resistance generator is formed only on the external surface of the case.

9. The body-insertable apparatus according to claim 1, wherein the suction operation generator includes a cam member that rotates about a predetermined shaft to change the shape of the soft tube member so that the soft tube member moves peristaltically due to the rotation; and a driving mechanism that supplies rotation torque to the cam member.

10. The body-insertable apparatus according to claim 1, wherein the soft tube member has check valves respectively formed near the suction-side opening and near the discharge-side opening, and the suction operation generator changes the shape of the soft tube so that a volume of a hollow area of the soft tube member between the check valves increases or decreases.

11. The body-insertable apparatus according to claim 1, further comprising:

a pressure detector that detects a pressure of the fluid sucked by the suction-side opening near the suction-side opening of the hollow area of the soft tube member; and a controller that controls driving state of the suction operation generator so that a detection result of the pressure detector is maintained at a predetermined value.

12. A body-insertable apparatus inserted into a subject for acquiring in-vivo information while moving in the subject, comprising:

an in-vivo information acquiring unit that acquires the in-vivo information;

an external case member that accommodates the in-vivo information acquiring unit, a suction-side opening being formed in a region of the external case member, and a discharge-side opening being formed in other region of the external case member;

a soft tube member that connects the suction-side opening to the discharge-side opening; and a displacement operation generator that changes a shape of the soft tube member so that an external fluid present near the suction-side opening is sucked via the suction-side opening and discharged from the discharge-side opening via the soft tube member, and changes at least one of a position and an orientation of the body-insertable apparatus by a reaction force of the suction operation and the discharge operation.

13. A body-insertable apparatus system, comprising:

a body-insertable apparatus inserted into a subject to acquire in-vivo information while moving in the subject and to transmit a radio signal including the in-vivo information acquired; and an external apparatus that receives the radio signal transmitted from the body-insertable apparatus, wherein the body-insertable apparatus includes an in-vivo information acquiring unit acquiring the in-vivo information;

an external case member accommodating the in-vivo information acquiring unit; and a moving-speed suppressing unit positioned inside or outside of the external case member to generate a predetermined suppressing force for suppressing a moving speed in between an inner wall of a passage route in the subject and the external case member, a soft tube member that connects a suction-side opening to a discharge-side opening;

a suction operation generator that changes a shape of the soft tube member so that external fluid present near the suction-side opening is sucked via the suction-side opening and discharged from the discharge-side opening via the soft tube member; and a controller that controls driving state of the suction operation generator so as to have a value determined by a predetermined control signal, and the external apparatus includes a receiving circuit that performs receiving processing of the radio signal received via a receiving antenna; and a signal processor that performs predetermined processing on a signal output from the receiving circuit to extract the in-vivo information, wherein the moving-speed suppressing unit includes an adhering mechanism that adheres to an inner wall of the passage route with a predetermined strength, and the external case member accommodates the adhering mechanism, wherein the suction-side opening is formed in a region of the external case member, the discharge-side opening is formed in other region of the external case member.

14. The body-insertable apparatus system according to claim 13, wherein the moving-speed suppressing unit includes a resistance generator formed on an external surface of the external case member to generate a resistance for blocking movement of the body-insertable apparatus by an interaction generated between a portion of the inner wall of the passage route brought into contact with the body-insertable apparatus and the body-insertable apparatus.

15. The body-insertable apparatus system according to claim 13, wherein the external device further includes a control signal generator that generates the control signal; and a transmitter that wirelessly transmits the control signal generated by the control signal generator, the body-insertable apparatus further includes a receiver that receives the radio signal transmitted from the transmitter; and a signal processor that extracts the control signal from the radio signal received by the receiver, and the controller performs control based the control signal.

* * * * *